US006677308B1

(12) United States Patent
Chandrakumar et al.

(10) Patent No.: US 6,677,308 B1
(45) Date of Patent: Jan. 13, 2004

(54) META-SUBSTITUTED PHENYLENE SULPHONAMIDE DERIVATIVES

(75) Inventors: Nizal Chandrakumar, Vernon Hills, IL (US); Michael Clare, Skokie, IL (US); Wendell Doubleday, Encinitas, CA (US); Alan F. Gasiecki, Vernon Hills, IL (US); Mark A. Russell, Gurnee, IL (US)

(73) Assignee: G. D. Searle & Co., Chicago, IL (US)

( * ) Notice: Subject to any disclaimer, the term of this patent is extended or adjusted under 35 U.S.C. 154(b) by 0 days.

(21) Appl. No.: 09/141,547

(22) Filed: Aug. 28, 1998

Related U.S. Application Data

(62) Division of application No. 08/824,626, filed on Mar. 27, 1997, now Pat. No. 5,843,906.
(60) Provisional application No. 60/014,415, filed on Mar. 26, 1996.

(51) Int. Cl.$^7$ .................................................. A61K 38/00
(52) U.S. Cl. ........................................ 514/19; 514/476
(58) Field of Search ..................................... 514/19, 476

(56) References Cited

FOREIGN PATENT DOCUMENTS

| EP | 0 222 608 A | 5/1987 | ......... C07C/129/12 |
| EP | 0 478 328 A1 | 4/1992 | ......... C07C/271/22 |
| EP | 0 478 363 A2 | 4/1992 | ......... C07D/211/22 |
| FR | 2 456 731 A | 12/1980 | ......... C07C/129/12 |
| WO | WO 92/08464 | 5/1992 | .......... A61K/31/55 |
| WO | WO 95/32710 | 12/1995 | .......... A61K/31/18 |

OTHER PUBLICATIONS

Fisher et al., "Inhibition of Osteoclastic Bone Resorption In Vivo by Echistatin, an 'Arginyl–Glycyl–Aspartyl' (RGD)–Containing Protein", *Endocrinology*, vol. 132, p. 1411–1413 (1993).
Brooks et al., "Requirement of Vascular Integrin $\alpha_v \beta_3$ for Angiogenesis" *Science*, vol. 264, pp. 569–571 (1994).
Brooks et al., "Integrin $\alpha_v \beta_3$ Antagonists Promote Tumor Regression by Inducing Apoptosis of Angiogenic Blood Vessels" *Cell*, vol. 79, pp. 1157–1164 (1994).
Seftor, et al., "Role of the $\alpha_v \beta_3$ Integrin in Human Melanoma Cell Invasion", *Proc. Natl. Acad. Sci. USA*, vol. 89, pp. 1557–1561 (1992).

*Primary Examiner*—Sheela Huff
(74) *Attorney, Agent, or Firm*—Cynthia Kovacevic; Rachel A. Polster

(57) ABSTRACT

The present invention relates to a class of compounds represented by the Formula I

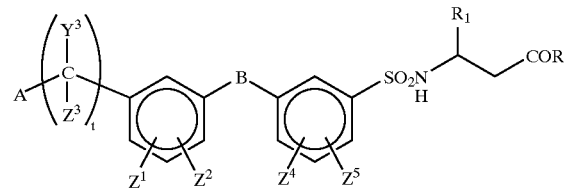

or a pharmaceutically acceptable salt thereof, pharmaceutical compositions comprising compounds of the Formula I, and methods of selectively inhibiting or antagonizing the $\alpha_v \beta_3$ integrin.

21 Claims, No Drawings

META-SUBSTITUTED PHENYLENE SULPHONAMIDE DERIVATIVES

This application is a divisional of U.S. Ser. No. 08/824,626, filed Mar. 27, 1997, now U.S. Pat. No. 5,843,906, which claims priority under 35 USC §119(e) of U.S. provisional application Serial No. 60/014,415 filed Mar. 26, 1996.

FIELD OF THE INVENTION

The present invention relates to pharmaceutical agents (compounds) which are useful as $\alpha_v\beta_3$ integrin antagonists or inhibitors and as such are useful in pharmaceutical compositions and in methods for treating conditions mediated by $\alpha_v\beta_3$ by inhibiting or antagonizing $\alpha_v\beta_3$ integrins.

BACKGROUND OF THE INVENTION

Integrins are a group of cell surface glycoproteins which mediate cell adhesion and therefore are useful mediators of cell adhesion interactions which occur during various biological processes. Integrins are heterodimers composed of noncovalently linked $\alpha$ and $\beta$ polypeptide subunits. Currently eleven different $\alpha$ subunits have been identified and six different $\beta$ subunits have been identified. The various $\alpha$ subunits can combine with various $\beta$ subunits to form distinct integrins.

The integrin identified as $\alpha_v\beta_3$ (also known as the vitronectin receptor) has been identified as an integrin which plays a role in various conditions or disease states including tumor metastasis, solid tumor growth (neoplasia), osteoporosis, Paget's disease, humoral hypercalcemia of malignancy, angiogenesis, including tumor angiogenesis, retinopathy, arthritis, including rheumatoid arthritis, periodontal disease, psoriasis and smooth muscle cell migration (e.g. restenosis). Additionally, it has been found that such agents would be useful as antivirals, antifungals and antimicrobials. Thus, compounds which selectively inhibit or antagonize $\alpha_v\beta_3$ would be beneficial for treating such conditions.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\beta_3$ as opposed to $\alpha_{IIb}\beta_3$.

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (Proc. Natl. Acad. Sci. USA, Vol. 89 (1992) 1557–1561) have shown that the $\alpha_v\beta_3$ integrin has a biological function in melanoma cell invasion. Montgomery et al., (Proc. Natl. Acad. Sci. USA, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The adhesion receptor integrin $\alpha_v\beta_3$ was identified as a marker of angiogenic blood vessels in chick and man and therefore such receptor plays a critical role in angiogenesis or neovascularization. Angiogenesis is characterized by the invasion, migration and proliferation of smooth muscle and endothelial cells. Antagonists of $\alpha_v\beta_3$ inhibit this process by selectively promoting apoptosis of cells in neovasculature. The growth of new blood vessels, or angiogenesis, also contributes to pathological conditions such as diabetic retinopathy (Adonis et al., Amer. J. Ophthal., Vol. 118, (1994) 445–450) and rheumatoid arthritis (Peacock et al., J. Exp. Med., Vol. 175, (1992), 1135–1138). Therefore, $\alpha_v\beta_3$ antagonists would be useful therapeutic targets for treating such conditions associated with neovascularization (Brooks et al., Science, Vol. 264, (1994), 569–571).

It has been reported that the cell surface receptor $\alpha_v\beta_3$ is the major integrin on osteoclasts responsible for attachment to bone. Osteoclasts cause bone resorption and when such bone resorbing activity exceeds bone forming activity it results in osteoporosis (a loss of bone), which leads to an increased number of bone fractures, incapacitation and increased mortality. Antagonists of $\alpha_v\beta_3$ have been shown to be potent inhibitors of osteoclastic activity both in vitro [Sato et al., J. Cell. Biol., Vol. 111 (1990) 1713–1723] and in vivo [Fisher et al., Endocrinology, Vol. 132 (1993) 1411–1413]. Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis.

The role of the $\alpha_v\beta_3$ integrin in smooth muscle cell migration also makes it a therapeutic target for prevention or inhibition of neointimal hyperplasia which is a leading cause of restenosis after vascular procedures (Choi et al., J. Vasc. Surg. Vol. 19(1) (1994) 125–34). Prevention or inhibition of neointimal hyperplasia by pharmaceutical agents to prevent or inhibit restenosis would be beneficial.

White (Current Biology, Vol. 3(9)(1993) 596–599) has reported that adenovirus uses $\alpha_v\beta_3$ for entering host cells. The integrin appears to be required for endocytosis of the virus particle and may be required for penetration of the viral genome into the host cell cytoplasm. Thus compounds which inhibit $\alpha_v\beta_3$ would find usefulness as antiviral agents.

SUMMARY OF THE INVENTION

The present invention relates to a class of compounds represented by the Formula I

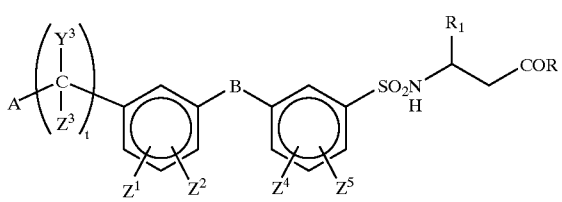

or a pharmaceutically acceptable salt thereof, wherein

B is selected from the group consisting of —CONR$^{50}$— and —SO$_2$NR$^{50}$—;

A is

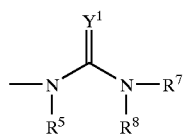

wherein $Y^1$ is selected from the group consisting of $N-R^2$, O, and S;

$R^2$ is selected from the group consisting of H; alkyl; aryl; hydroxy; alkoxy; cyano; nitro; amino; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy and phenyl;

or $R^2$ taken together with $R^7$ forms a 5 membered heteroaromatic ring;

or $R^2$ taken together with $R^7$ forms a 5 membered heteroaromatic ring fused with a phenyl group;

$R^7$ when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; $-SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

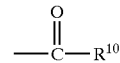

wherein $R^{10}$ is defined above;

or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, alkyl, alkenyl, alkynyl, benzyl, and phenethyl;

or

A is

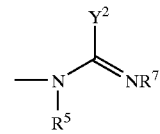

wherein $Y^2$ is selected from the group consisting of H, alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkynyl; alkenyl; $-S-R^9$ and $-O-R^9$ wherein $R^9$ is selected from the group consisting of H; alkyl; aralkyl; aryl; alkenyl; and alkynyl; or $R^9$ taken together with $R^7$ forms a 4–12 membered mononitrogen containing sulfur or oxygen containing heterocyclic ring; and $R^5$ and $R^7$ are as defined above;

or $Y^2$ (when $Y^2$ is carbon) taken together with $R^7$ forms a 4–12 membered mononitrogen containing ring optionally substituted with alkyl, aryl or hydroxy;

$Z^1$, $Z^2$, $Z^4$ and $Z^5$ are independently selected from the group consisting of H; alkyl; hydroxy; alkoxy; aryloxy; aralkoxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles; and A, wherein A is defined above;

$R^{50}$ is selected from the group consisting of H and alkyl;

$R^1$ is selected from the group consisting of H, alkyl, alkenyl, alkynyl, aryl and aryl, optionally substituted with one or more substituent selected from the group consisting of halogen, haloalkyl, hydroxy, alkoxy, aryloxy, aralkoxy, amino, aminoalkyl, carboxyl derivatives, cyano and nitro;

t is an integer 0, 1 or 2;

R is X—$R^3$ wherein X is selected from the group consisting of O, S and $NR^4$, wherein $R^3$ and $R^4$ are independently selected from the group consisting of hydrogen; alkyl; alkenyl; alkynyl; haloalkyl; aryl; aralalkyl; sugars; steroids and in the case of the free acid, all pharmaceutically acceptable salts thereof; and $Y^3$ and $Z^3$ are independently selected from the group consisting of H, alkyl, aryl, cycloalkyl and aralkyl.

It is another object of the invention to provide pharmaceutical compositions comprising compounds of the Formula I. Such compounds and compositions are useful in selectively inhibiting or antagonizing the $\alpha_v\beta_3$ integrin and therefore in another embodiment the present invention relates to a method of selectively inhibiting or antagonizing the $\alpha_v\beta_3$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials.

DETAILED DESCRIPTION

The present invention relates to a class of compounds represented by the Formula I, described above.

A preferred embodiment of the present invention is a compound of the Formula II

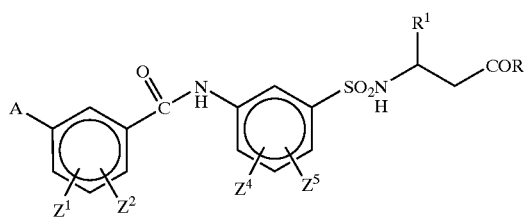

Another preferred embodiment of the present invention is a compound of the Formula III

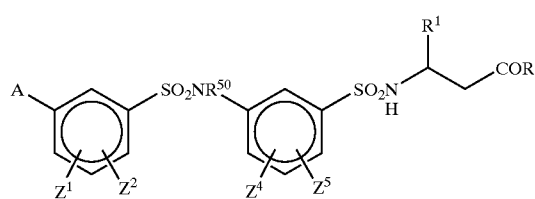

The invention further relates to pharmaceutical compositions containing therapeutically effective amounts of the compounds of Formulas I–III.

The invention also relates to a method of selectively inhibiting or antagonizing the $\alpha_v\beta_3$ integrin and more specifically relates to a method of inhibiting bone resorption, periodontal disease, osteoporosis, humoral hypercalcemia of malignancy, Paget's disease, tumor metastasis, solid tumor growth (neoplasia), angiogenesis, including tumor angiogenesis, retinopathy including diabetic retinopathy, arthritis, including rheumatoid arthritis, smooth muscle cell migration and restenosis by administering a therapeutically effective amount of a compound of the Formula I–III to achieve such inhibition together with a pharmaceutically acceptable carrier.

The following is a list of definitions of various terms used herein:

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon-carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The term "cycloalkyl" as used herein means saturated or partially unsaturated cyclic carbon radicals containing 3 to about 8 carbon atoms and more preferably 4 to about 6 carbon atoms. Examples of such cycloalkyl radicals include cyclopropyl, cyclopropenyl, cyclobutyl, cyclopentyl, cyclohexyl, 2-cyclohexen-1-yl, and the like.

The term "aryl" as used herein denotes aromatic ring systems composed of one or more aromatic rings. Preferred aryl groups are those consisting of one, two or three aromatic rings. The term embraces aromatic radicals such as phenyl, pyridyl, naphthyl, thiophene, furan, biphenyl and the like.

As used herein, the term "cyano" is represented by a radical of the formula

The terms "hydroxy" and "hydroxyl" as used herein are synonymous and are represented by a radical of the formula

The term "lower alkylene" or "alkylene" as used herein refers to divalent linear or branched saturated hydrocarbon radicals of 1 to about 6 carbon atoms.

As used herein the term "alkynylene" or "lower alkynylene" refers to an alkylene radical wherein at least one bond between the carbon atoms is unsaturated and such unsaturation forms a triple bond.

As used herein the term "alkenylene" or "lower alkenylene" refers to an alkylene radical wherein at least one bond between the carbon atoms is unsaturated and such unsaturation produces a double bond in cis or transconformation.

As used herein the term "alkoxy" refers to straight or branched chain oxy containing radicals of the formula —OR$^{20}$, wherein R$^{20}$ is an alkyl group as defined above. Examples of alkoxy groups encompassed include methoxy, ethoxy, n-propoxy, n-butoxy, isopropoxy, isobutoxy, sec-butoxy, t-butoxy and the like.

As used herein the terms "arylalkyl" or "aralkyl" refer to a radical of the formula

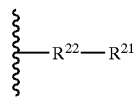

wherein R$^{21}$ is aryl as defined above and R$^{22}$ is an alkylene as defined above. Examples of aralkyl groups include benzyl, pyridylmethyl, naphthylpropyl, phenethyl and the like.

As used herein the term "aralkoxy" or "arylakoxy" refers to a radical of the formula

wherein R$^{53}$ is aralkyl as defined above.

As used herein the term "nitro" is represented by a radical of the formula

As used herein the term "halo" or "halogen" refers to bromo, chloro, fluoro or iodo.

As used herein the term "haloalkyl" refers to alkyl groups as defined above substituted with one or more of the same or different halo groups at one or more carbon atom. Examples of haloalkyl groups include trifluoromethyl, dichloroethyl, fluoropropyl and the like.

As used herein the term "carboxyl" or "carboxy" refers to a radical of the formula —COOH.

As used herein the term aminoalkyl" refers to a radical of the formula —R$^{54}$—NH$_2$ wherein R$^{54}$ is lower alkylene as defined above.

As used herein the term "carboxyl derivative" refers to a radical of the formula

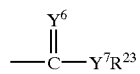

wherein Y$^6$ and Y$^7$ are independently selected from the group consisting of O, N or S and R$^{23}$ is selected from the group consisting of H, alkyl, aralkyl or aryl as defined above.

As used herein the term "amino" is represented by a radical of the formula —NH$_2$.

As used herein the term "alkylsulfonyl" or "alkylsulfone" refers to a radical of the formula

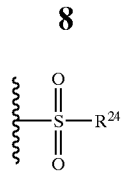

wherein R$^{24}$ is alkyl as defined above.

As used herein the term "alkylthio" refers to a radical of the formula —SR$^{24}$ wherein R$^{24}$ is alkyl as defined above.

As used herein the term "sulfonic acid" refers to a radical of the formula

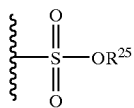

wherein R$^{25}$ is H, alkyl or aryl as defined above.

As used herein the term "sulfonamide" refers to a radical of the formula

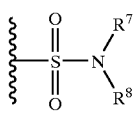

wherein R$^7$ and R$^8$ are as defined above.

As used herein the term "fused aryl" refers to an aromatic ring such as the aryl groups defined above fused to one or more phenyl rings. Embraced by the term "fused aryl" is the radical naphthyl.

As used herein the terms "monocyclic heterocycle" or "monocyclic heterocyclic" refer to a monocyclic ring containing from 4 to about 12 atoms, and more preferably from 5 to about 10 atoms, wherein 1 to 3 of the atoms are heteroatoms selected from the group consisting of oxygen, nitrogen and sulfur with the understanding that if two or more different heteroatoms are present at least one of the heteroatoms must be nitrogen. Representative of such monocyclic heterocycles are imidazole, furan, pyridine, oxazole, pyran, triazole, thiophene, pyrazole, thiazole, thiadiazole, and the like.

As used herein the term "fused monocyclic heterocycle" refers to a monocyclic heterocycle as defined above with a benzene fused thereto. Examples of such fused monocyclic heterocycles include benzofuran, benzopyran, benzodioxole, benzothiazole, benzothiophene, benzimidazole and the like.

As used herein the term "methylenedioxy" refers to the radical

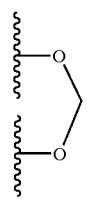

and the term "ethylenedioxy" refers to the radical

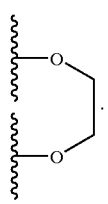

As used herein the term "4–12 membered dinitrogen containing heterocycle refers to a radical of the formula

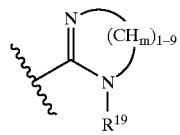

wherein m is 1 or 2 and $R^{19}$ is H, alkyl, aryl, or aralkyl and more preferably refers to 4–9 membered ring and includes rings such as imidazoline.

As used herein the term "5-membered heteroaromatic ring" includes for example a radical of the formula

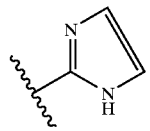

and "5-membered heteroaromatic ring fused with a phenyl" refers to such a "5-membered heteroaromatic ring" with a phenyl fused thereto. Representative of such 5-membered heteroaromatic rings fused with a phenyl is benzimidazole.

As used herein the term "bicycloalkyl" refers to a bicyclic hydrocarbon radical containing 6 to about 12 carbon atoms which is saturated or partially unsaturated.

As used herein the term "acyl" refers to a radical of the formula

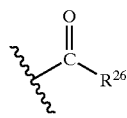

wherein $R^{26}$ is alkyl, alkenyl, alkynyl, aryl or aralkyl as defined above. Encompassed by such radical are the groups acetyl, benzoyl and the like.

As used herein the term "thio" refers to a radical of the formula

As used herein the term "sulfonyl" refers to a radical of the formula

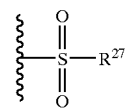

wherein $R^{27}$ is alkyl, aryl or aralkyl as defined above.

As used herein the term "haloalkylthio" refers to a radical of the formula —S—$R^{28}$ wherein $R^{28}$ is haloalkyl as defined above.

As used herein the term "aryloxy" refers to a radical of the formula

wherein $R^{29}$ is aryl as defined above.

As used herein the term "acylamino" refers to a radical of the formula

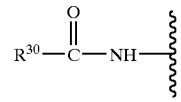

wherein $R^{30}$ is alkyl, aralkyl or aryl as defined above.

As used herein the term "amido" refers to a radical of the formula

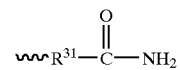

wherein $R^{31}$ is a bond or alkylene as defined above.

As used herein the term "alkylamino" refers to a radical of the formula —NH$R^{32}$ wherein $R^{32}$ is alkyl as defined above.

As used herein the term "dialkylamino" refers to a radical of the formula —N$R^{33}R^{34}$ wherein $R^{33}$ and $R^{34}$ are the same or different alkyl groups as defined above.

As used herein the term "trifluoromethyl" refers to a radical of the formula

As used herein the term "trifluoroalkoxy" refers to a radical of the formula

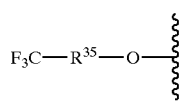

wherein $R^{35}$ is a bond or an alkylene as defined above.

As used herein the term "alkylaminosulfonyl" refers to a radical of the formula

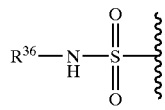

wherein $R^{36}$ is alkyl as defined above.

As used herein the term "alkylsulfonylamino" refers to a radical of the formula

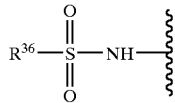

wherein $R^{36}$ is alkyl as defined above.

As used herein the term "trifluoromethylthio" refers to a radical of the formula

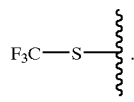

As used herein the term "trifluoromethylsulfonyl" refers to a radical of the formula

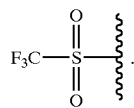

As used herein the term "4–12 membered mono-nitrogen containing monocyclic or bicyclic ring" refers to a saturated or partially unsaturated monocyclic or bicyclic ring of 4–12 atoms and more preferably a ring of 4–9 atoms wherein one atom is nitrogen. Such rings may optionally contain additional heteroatoms selected from nitrogen, oxygen or sulfur. Included within this group are morpholine, piperidine, piperazine, thiomorpholine, pyrrolidine, proline, azacycloheptene and the like.

As used herein the term "benzyl" refers to the radical

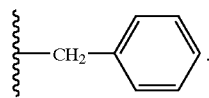

As used herein the term "phenethyl" refers to the radical

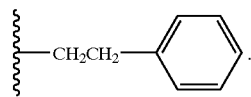

As used herein the term "4–12 membered mono-nitrogen containing sulfur or oxygen containing heterocyclic ring" refers to a ring consisting of 4 to 12 atoms and more preferably 4 to 9 atoms wherein at least one atom is a nitrogen and at least one atom is oxygen or sulfur. Encompassed within this definition are rings such as thiazoline and the like.

As used herein the term "arylsulfonyl" or "arylsulfone" refers to a radical of the formula

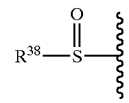

wherein $R^{37}$ is aryl as defined above.

As used herein the terms "alkylsulfoxide" or "arylsulfoxide" refer to radicals of the formula

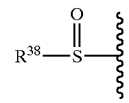

wherein $R^{38}$ is, respectively, alkyl or aryl as defined above.

As used herein the term "phosphonic acid derivative" refers to a radical of the formula

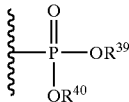

wherein $R^{39}$ and $R^{40}$ are the same or different H, alkyl, aryl or aralkyl.

As used herein the term "phosphinic acid derivatives" refers to a radical of the formula

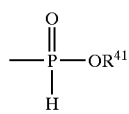

wherein $R^{41}$ is H, alkyl, aryl or aralkyl as defined above.

As used herein the term "arylthio" refers to a radical of the formula

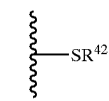

wherein $R^{42}$ is aryl as defined above.

As used herein the term "monocyclic heterocycle thio" refers to a radical of the formula

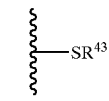

wherein $R^{43}$ is a monocyclic heterocycle radical as defined above.

As used herein the terms "monocyclic heterocycle sulfoxide" and "monocyclic heterocycle sulfone" refer, respectively, to radicals of the formula

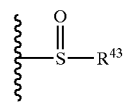

and

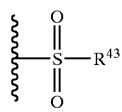

wherein $R^{43}$ is a monocyclic heterocycle radical as defined above.

The term "composition" as used herein means a product which results from the mixing or combining of more than one element or ingredient.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:

$^1$H-NMR=proton nuclear magnetic resonance
AcOH=acetic acid
$BH_3$-THF=borane-tetrahydrofuran complex
BOC=tert-butoxycarbonyl
Cat.=catalytic amount
$CH_2Cl_2$=dichloromethane
$CH_3CN$=acetonitrile
$CH_3I$=iodomethane
CHN analysis=carbon/hydrogen/nitrogen elemental analysis
CHNCl analysis=carbon/hydrogen/nitrogen/chlorine elemental analysis
CHNS analysis=carbon/hydrogen/nitrogen/sulfur elemental analysis
DCC=1,3-dicyclohexylcarbodiimide
DIEA=diisopropylethylamine
DMA=N,N-dimethylacetamide
DMAC=Dimethylacetamide
DMAP=4-(N,N-dimethylamino)pyridine
DMF=N,N-dimethylformamide
DSC=disuccinyl carbonate
EDCI=1-(3-dimethylaminopropyl)-3-ethylcarbodiimide hydrochloride
$Et_2O$=diethyl ether
$Et_3N$=triethylamine
EtOAc=ethyl acetate
EtOH=ethanol
FAB MS=fast atom bombardment mass spectroscopy
g=gram(s)
GIHA HCl=meta-guanidino-hippuric acid hydrochloride
GIHA=meta-guanidino-hippuric acid
HPLC=high performance liquid chromatography
IBCF=isobutylchloroformate
$K_2CO_3$=potassium carbonate
KOH=potassium hydroxide
LiOH=lithium hydroxide
MCPBA=m-chloroperoxybenzoic acid or m-chloroperbenzoic acid
MeOH=methanol
MesCl=methanesulfonylchloride
mg=milligram
$MgSO_4$=magnesium sulfate
ml=milliliter
mL=milliliter
MS=mass spectroscopy
$N_2$=nitrogen
$NaCNBH_3$=sodium cyanoborohydride
$Na_2PO_4$=sodium phosphate
$Na_2SO_4$=sodium sulfate
$NaHCO_3$=sodium bicarbonate
NaOH=sodium hydroxide
$NH_4HCO_3$=ammonium bicarbonate
$NH_4^+HCO_2$=ammonium formate
NMM=N-methyl morpholine
NMR=nuclear magnetic resonance
RPHPLC=reverse phase high performance liquid chromatography
RT=room temperature
KSCN=potassium thiocyanate
Pd/C=palladium on carbon
Bn=benzyl
Et=ethyl
Me=methyl
Ph=phenyl
$NEt_3$=triethylamine
t-BOC=tert-butoxycarbonyl
TFA=trifluoroacetic acid
THF=tetrahydrofuran
Δ=heating the reaction mixture As used herein HPLC-Method 1 refers to reverse phase C-18 functionalized silica gel column (50×300 mm) using a linear gradient of 95% 0.6% TFA/water:5% $CH_3CN$ to 60% 0.6% TFA/water:40% $CH_3CN$ with a flow rate of 80 ml/minute.

The compounds as shown in Formulas I–III can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of Formula I with an acid whose anion is generally considered suitable for human consumption. Examples of pharmacologically acceptable salts include the hydrochloride, hydrobromide, hydroiodide, sulfate, phosphate, acetate, propionate, lactate, maleate, malate, succinate, tartrate salts and the like. All of the pharmacologically acceptable salts may be prepared by conventional means. (See Berge et al., *J Pharm. Sci.*, 66(1), 1–19 (1977) for additional examples of pharmaceutically acceptable salts.)

For the selective inhibition or antagonism of $\alpha_v\beta_3$ integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, infusion techniques or intraperitonally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by selectively inhibiting or antagonizing the $\alpha_v\beta_3$ cell surface receptor which method comprises administering a therapeutically effective amount of a compound selected from the class of compounds depicted in Formulas I–III, wherein one or more compounds of the Formulas I–III is administered in association with one or more non-toxic, pharmaceutically acceptable carriers and/or diluents and/or adjuvants (collectively referred to herein as "carrier" materials) and if desired other active ingredients. More specifically, the present invention provides a method for inhibition of the $\alpha_v\beta_3$ cell surface receptor. Most preferably the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, inhibiting arthritis, psoriasis and periodontal disease, and inhibiting smooth muscle cell migration including restenosis.

Based upon standard laboratory experimental techniques and procedures well known and appreciated by those skilled in the art, as well as comparisons with compounds of known usefulness, the compounds of Formula I can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

Treatment of a patient afflicted with one of the pathological conditions comprises administering to such a patient an amount of compound of the Formula I which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

As stated previously, the compounds of the invention can be used in a variety of biological, prophylactic or therapeutic areas. It is contemplated that these compounds are useful in prevention or treatment of any disease state or condition wherein the $\alpha_v\beta_3$ integrin plays a role.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 1000 mg per kilogram of body weight per day are useful in the treatment of the above-indicated conditions and more preferably of the order from about 0.01 mg to about 100 mg/kg of body weight.

The active ingredient administered by injection is formulated as a composition wherein, for example, saline, dextrose or water may be used as a suitable carrier. A suitable daily dose would typically be about 0.01 to 100 mg/kg body weight injected per day in multiple doses depending on the factors listed above and more preferably from about 0.01 to about 10 mg/kg body weight.

For administration to a mammal in need of such treatment, the compounds in a therapeutically effective amount are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

The general synthetic sequences for preparing the compounds useful in the present invention are outlined in Schemes I–VI. Both an explanation of, and the actual procedures for, the various aspects of the present invention are described where appropriate. The following Schemes and Examples are intended to be merely illustrative of the present invention, and not limiting thereof in either scope or spirit. Those of skill in the art will readily understand that known variations of the conditions and processes described in the Schemes and Examples can be used to perform the process of the present invention.

Unless otherwise indicated all starting materials and equipment employed were commercially available.

SCHEME I

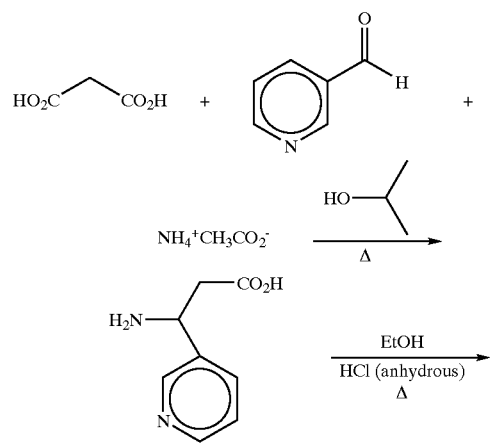

-continued

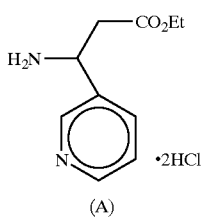

(A)

Schemes I–VI are illustrative of methodology useful for preparing various compounds of the present invention. Such methodology is more specifically defined in the examples which follow. Such methodology can be modified by one skilled in the art, substituting known reagents and conditions from conventional methodology to produce the desired compounds.

Scheme I describes a synthesis of a pyridyl β-aminoacid which can be used to synthesize compounds of the present invention wherein $R^1$ is pyridyl. The reaction can be modified using conventional methodology to prepare other aromatic, alkyl or heterocyclic substituted β-amino acids by substitution of the pyridyl carboxaldehyde with any other appropriate aldehyde. Briefly, in Scheme I to pyridinecarboxaldehyde in isopropanol is added ammonium acetate followed by malonic acid. The reaction mixture is stirred at reflux, the resulting precipitate filtered and washed with hot isopropanol and dried to yield 3-amino-3-(3-pyridyl) propionic acid. The ethyl ester is synthesized by heating this acid in excess ethanol in the presence of excess HCl gas.

Additionally, β-amino acids which are useful in the present invention are accessible through modified Knoevenagel reactions (Secor, H. V.; Edwards, W. B. J. *J. Org. Chem.* 1979, 44, 3136–40; Bellasoued, M.; Arous-Chtar, R.; Gaudemar, M. J.; *J. Organometal. Chem.* 1982, 231, 185–9), through Reformatski reaction with Schiff bases (Furukawa, M.; Okawara, T.; Noguchi, Y.; Terawaki, Y. *Chem. Pharm. Bull.* 1978, 26, 260), Michael addition into an acrylic derivative (Davies, S. G.; Ichihara, O. *Tetrahedron:Asymmetry* 1991, 2, 183–6; Furukawa, M.; Okawara, T R.; Terawaki, Y. *Chem. Pharm. Bull.*, 1977, 25, 1319–25). More recent methods include the use of organometallic reagents in Pd or Zn mediated couplings (Konopelski, J.; Chu, K. S.; Negrete, G. R. *J. Org. Chem.* 1991, 56, 1355; Mokhallalati, M. K.; Wu, M-J.; Prigden, L. N. *Tetrahedron Lett.* 1993, 34, 47–50) to complement more traditional reactions such as reductive amination of β-ketoesters.

The racemic beta-alkyl beta amino esters can also conveniently be prepared from the corresponding beta lactam by treatment with anhydrous HCl gas in ethanol. The beta lactams were prepared from the corresponding alkene and chlorosulfonyl isocyanate (Szabo, W. A. *Aldrichimica Acta*, 1977, 23 and references cited therein). The latter method is useful for the preparation of α and β-substituted β-aminoacids. (Manhas, M. S.; Wagle, D. R.; Chong, J.; Bose, A. K. *Heterocycles*, 1988, 27, 1755.) Another route to α-substituted β-aminoacids is the Raney Nickel reduction of cyanoacetic esters at temperatures ranging between 20 and 80° C. and at 20 to 100 atm pressure (Testa, E.; Fontanella, L.; Fava, F. *Fermaco Ed. Sci.*, 1958, 13, 152; Testa, E.; Fontanella, L. *Annalen* 1959, 625, 95). Also, a number of procedures are available for the preparation of β-aminoacids by reduction of hydrazones of keto-acids (Gottijes, J.; Nomte, W. Th. *Rec. Trav. Chem.* 1953, 72, 721), oximes (Anziegin, A.; Gulewivich, W. *Z. Physiol. Chem.*, 1926, 158, 32) and nitropropionic acids. Purification of final compounds is usually by reverse phase high performance liquid chromatography (RP HPLC) [High Performance Liquid Chromatography Protein and Peptide Chemistry, F. Lottspeich, A. Henscher, K. P. Hupa, (eds.) Walter DeGruyter, New York, 1981] or crystallization.

SCHEME II

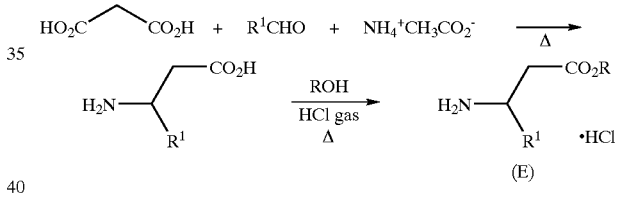

SCHEME III

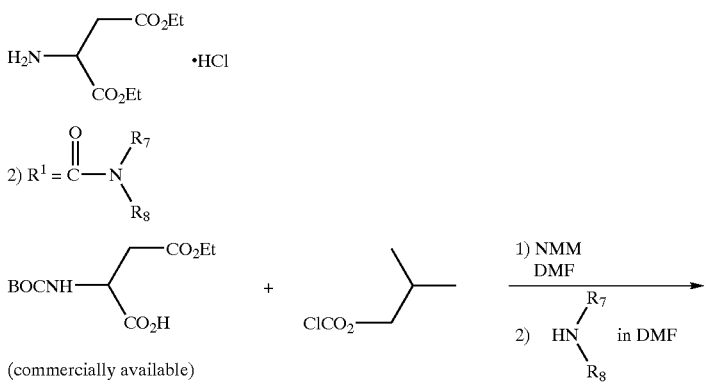

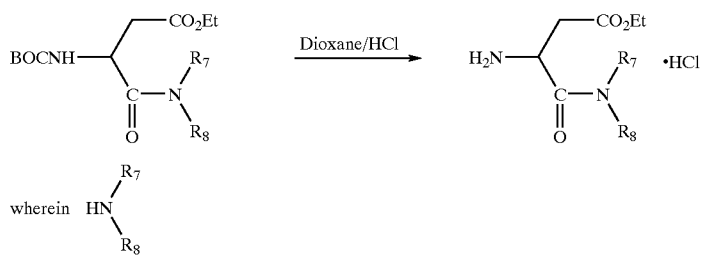
wherein $HN\overset{R_7}{\underset{R_8}{\diagup}}$
denotes an amino acid, the amino acid being protected with the appropriate protecting groups.
Additional methodologies for further $R^1$ groups are as follows:
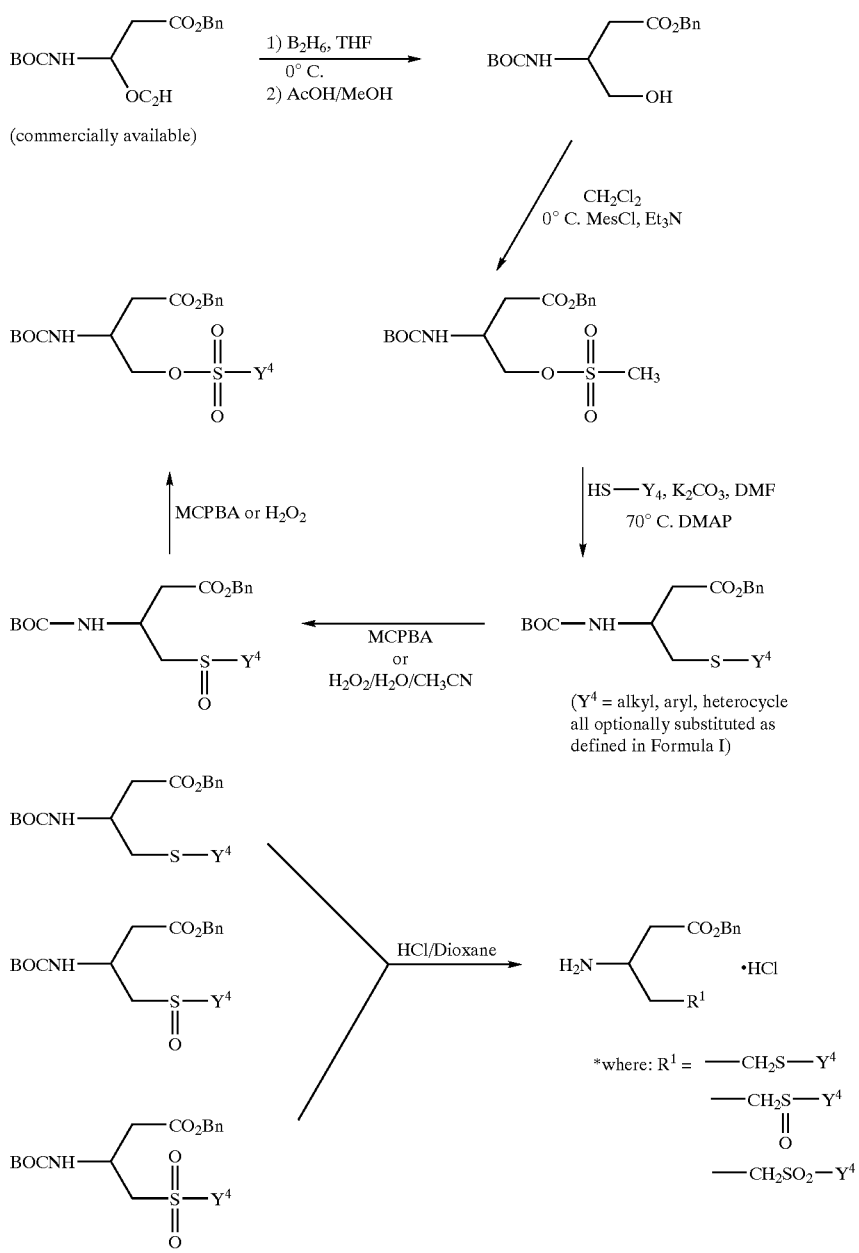
In a similiar manner, compounds of the present invention wherein $R^1$ is substituted alkyl can be synthesized in the following manner:

-continued
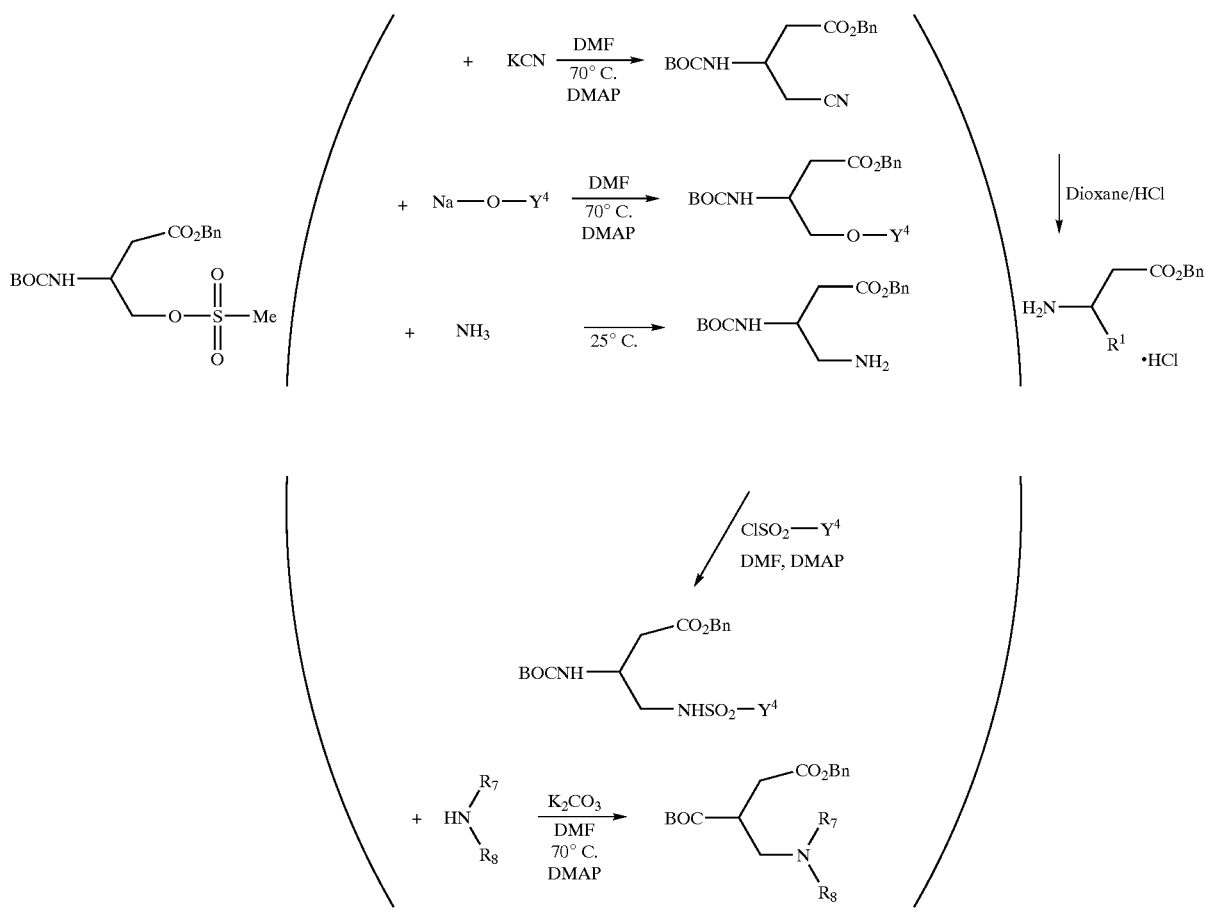
SCHEME IV
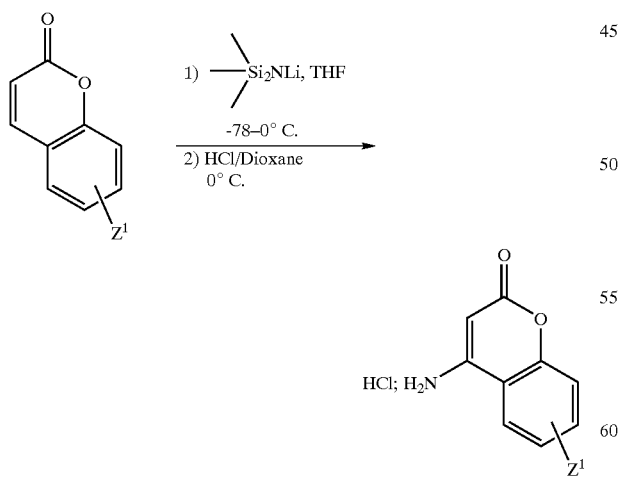
Scheme IV represents the synthesis of aminohydrocoumarins (see J. Rico, *Tett. Let.*, 1994, 35, 6599–6602) which are readily opened to form $R^1$ being an orthohydroxyphenyl moiety, further substituted by $Z^1$.
SCHEME V
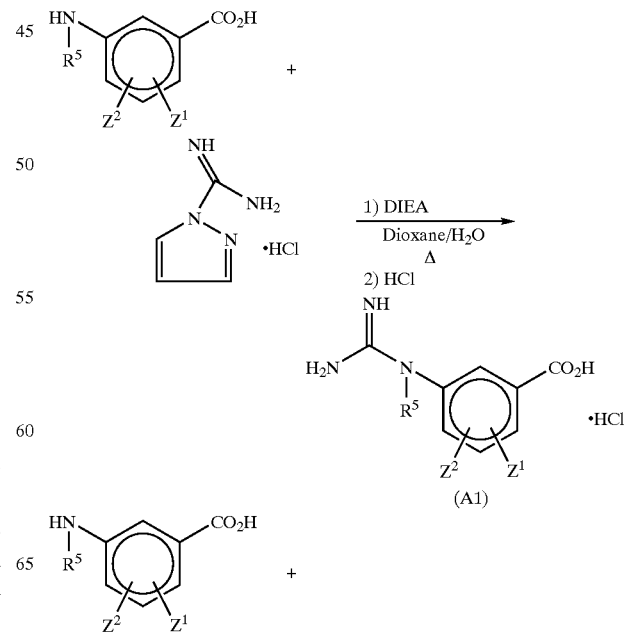

-continued
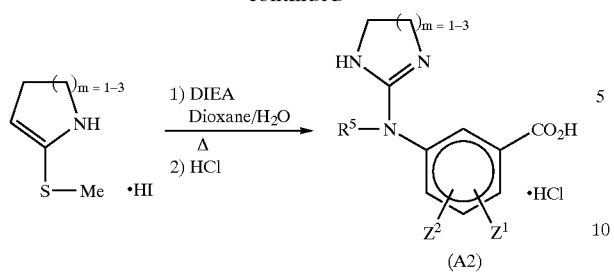
(A2)
(A3)
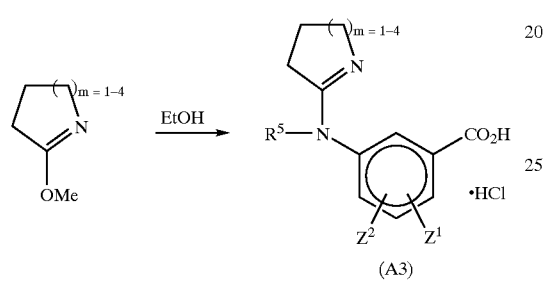
(A4)
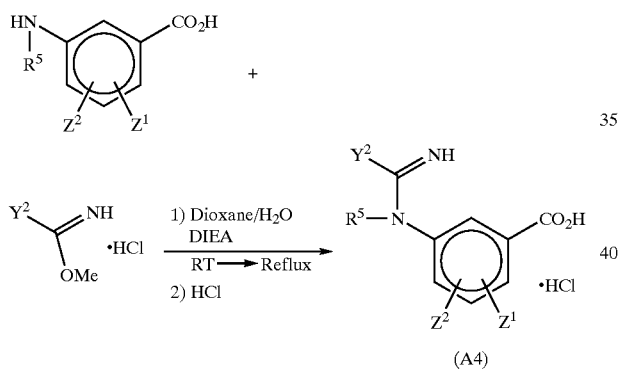
(A5)
(A5) + R⁹—I $\xrightarrow{\text{THF}\ \Delta}$ 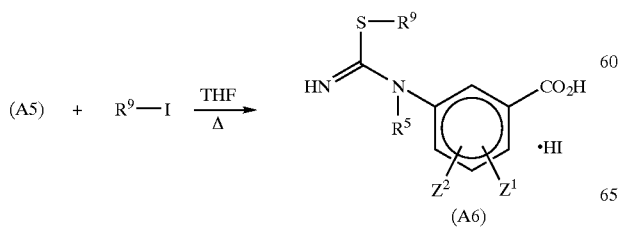
(A6)
-continued
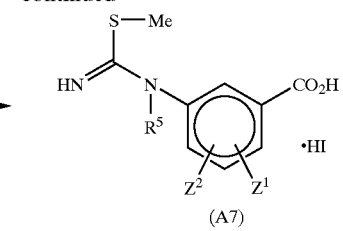
(A7)
(A7) + HN(R⁷)(R⁸) $\xrightarrow[\text{2) HCl}]{\text{1) DIEA Dioxane/H}_2\text{O}}$
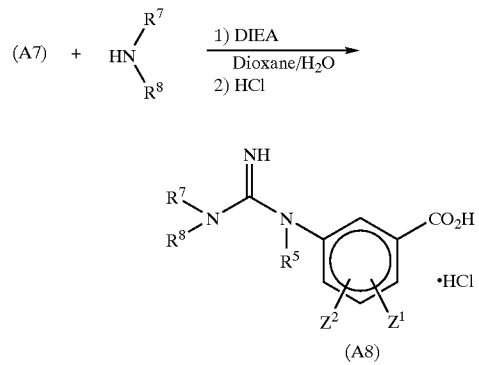
(A8)
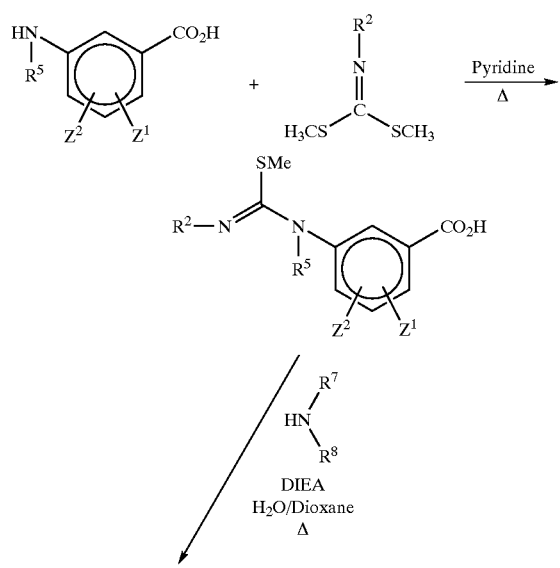
(A9)
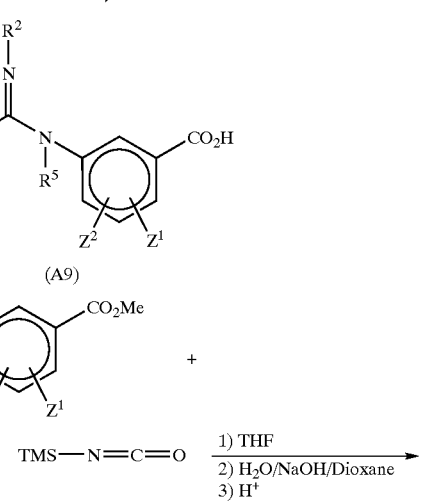

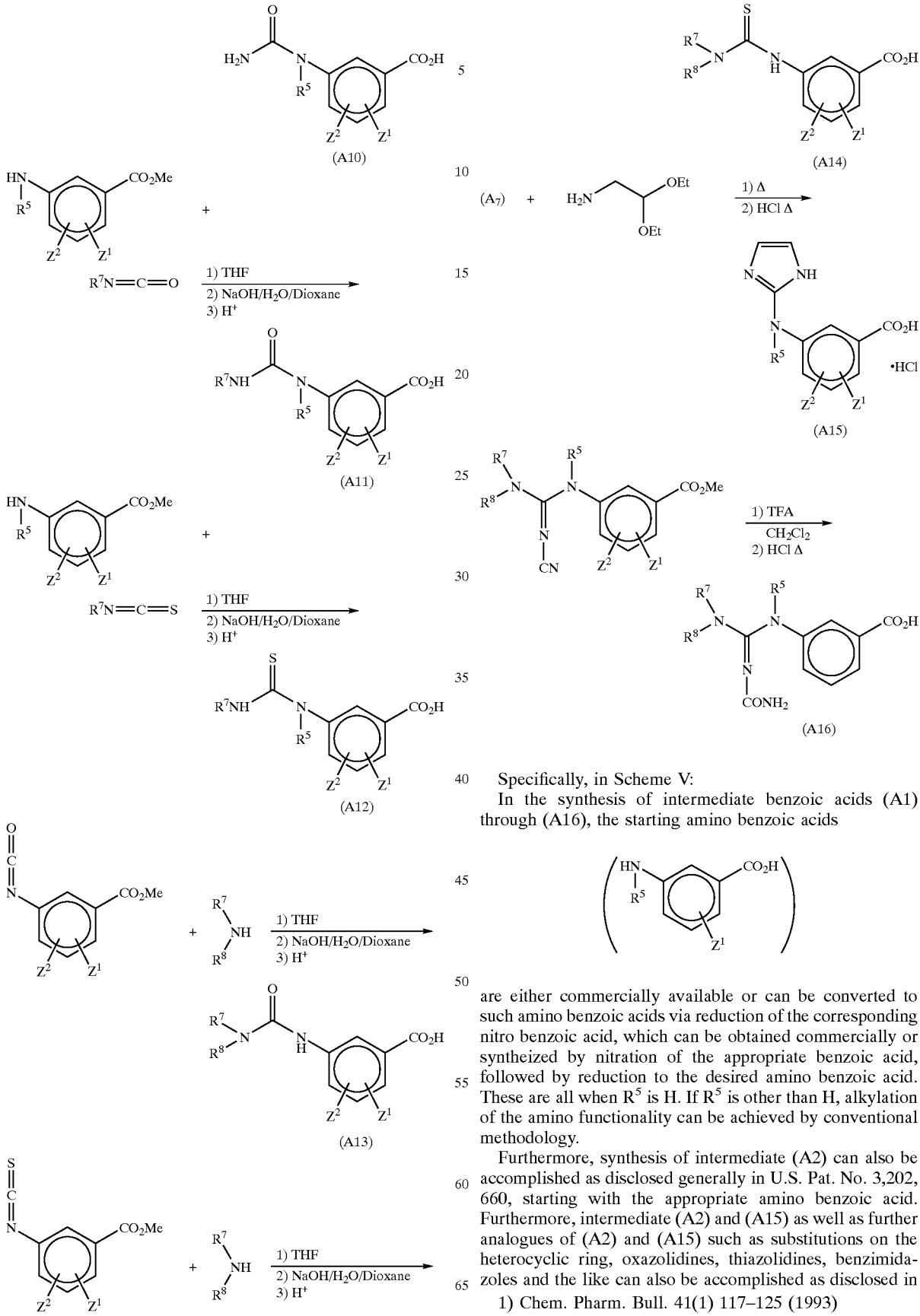

Specifically, in Scheme V:
In the synthesis of intermediate benzoic acids (A1) through (A16), the starting amino benzoic acids are either commercially available or can be converted to such amino benzoic acids via reduction of the corresponding nitro benzoic acid, which can be obtained commercially or syntheized by nitration of the appropriate benzoic acid, followed by reduction to the desired amino benzoic acid. These are all when $R^5$ is H. If $R^5$ is other than H, alkylation of the amino functionality can be achieved by conventional methodology.

Furthermore, synthesis of intermediate (A2) can also be accomplished as disclosed generally in U.S. Pat. No. 3,202,660, starting with the appropriate amino benzoic acid. Furthermore, intermediate (A2) and (A15) as well as further analogues of (A2) and (A15) such as substitutions on the heterocyclic ring, oxazolidines, thiazolidines, benzimidazoles and the like can also be accomplished as disclosed in
1) Chem. Pharm. Bull. 41(1) 117–125 (1993)
2) Chem. Pharm. Bull. 33(10) 4409–4421 (1985)

3) J. Med. Chem. 18 (1), 90–99 (1975).

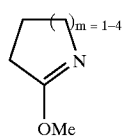

used in the synthesis of intermediates (A3), can be synthesized from

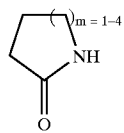

and $(Me)_3OBF_4$ in dichloromethane.

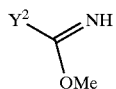

used in the synthesis of intermediate (A4), can be synthesized from $Y^2$—CN and MeOH (1 equivalent) and HCl gas (1 equivalent) in heptane.

All other reagents in Scheme I are either commercially available or readily synthesized by methodologies known by those skilled in the art.

When $R^{50}$ is not H, the appropriate nitrogen can be alkylated in an appropriate step by methodology known to those skilled in the art. Alternate acid derivatives R are synthesized by methodologies known to those skilled in the art.

To synthesize compounds wherein

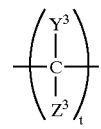

where t=1 and $Y^3$ and $Z^3$ are both hydrogen:

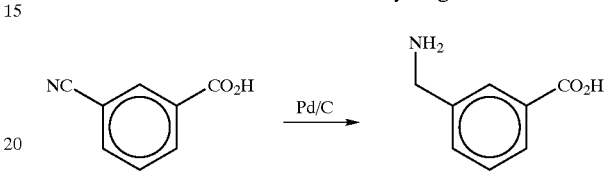

which is then treated in the same manner of further derivatization as exemplified in the previous schemes for:

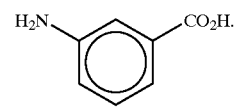

SCHEME VI

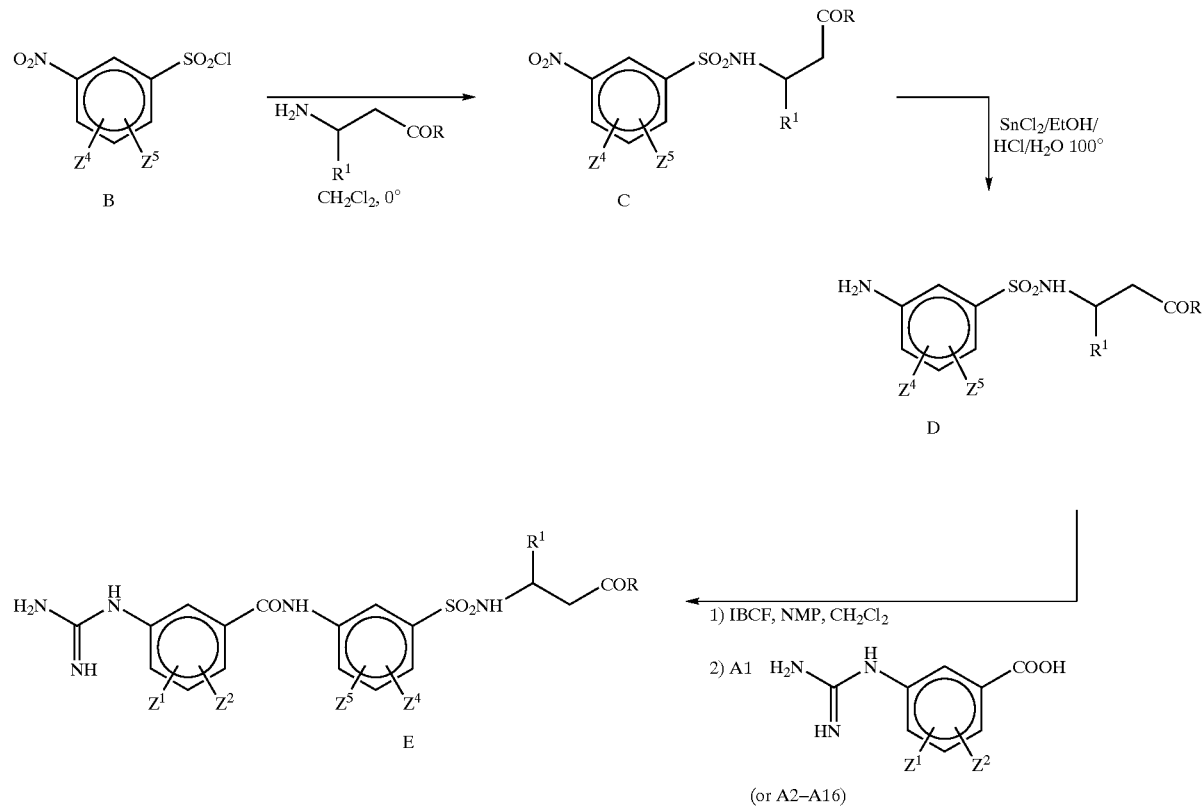

-continued

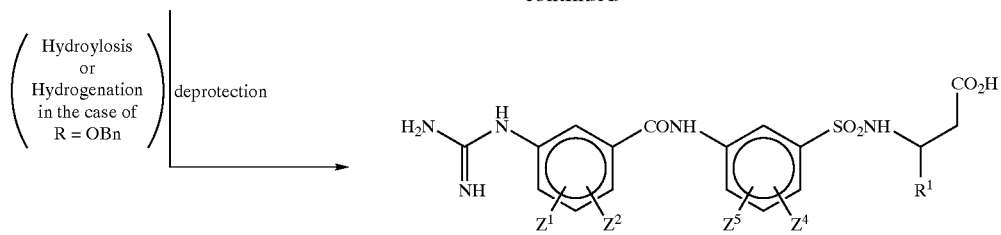

Compounds of the present invention may be prepared as follows:

3-Nitrophenylsulphonylchloride B can be coupled to β-amino acids (as prepared in Schemes I–IV) to afford adduct C. Reduction of C (SnCl$_2$, EtOH, HCl, H$_2$O, 100°) affords aniline D. Aniline D can be coupled to intermediates (A1–16) as prepared in Scheme V using well known and standard coupling procedures, followed by hydroylosis (or deprotection) of the resulting ester to afford compounds of the present invention.

EXAMPLE A

3-Guanidinobenzoic Acid Hydrochloride

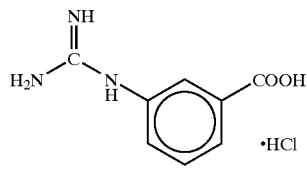

To 3,5-dimethylpyrazole-1-carboxamidine nitrate (6 g, 0.03 mole) (Aldrich) and diisopropylamine (3.8 g, 0.03 mole) in dioxane (20 ml) and H$_2$O (10 ml) was added 3-aminobenzoic acid (2.7 g, 0.02 mole). The reaction was stirred at reflux for 2.5 hours then overnight at room temperature. The resulting precipitate was filtered, washed with dioxane/H$_2$O and dried. The precipitate was then slurried in H$_2$O and acidified with concentrated HCl until a solution formed. The solvent was removed under vacuum and the residue was slurried twice in ether (ether decanted off). The product was dried under vacuum to yield 3-guanidinobenzoic acid hydrochloride (1.77 g) as a white solid. MS and NMR were consistent with the desired structure.

EXAMPLE B 3-(1-aza-2-Amino-1-cycloheptenyl)benzoic Acid Hydrochloride

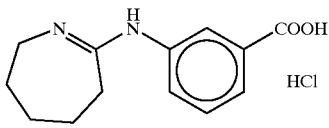

To 1-aza-2-methoxy-1-cycloheptene (3.67 g, 0.0288 mole) (Aldrich) in absolute ethanol (20 ml) was added 3-aminobenzoic acid hydrochloride (5 g, 0.0288 mole). A solution quickly formed. The reaction mixture was stirred overnight at room temperature. The resulting precipitate was filtered, washed with ether and dried under vacuum to yield 3-(1-aza-2-amino-1-cycloheptene)benzoic acid (4.9 g).

EXAMPLE C 3-(1-aza-2-Amino-1-cycloheptenyl)-5-trifluoromethylbenzoic Acid Hydrochloride

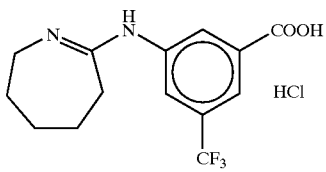

The title compound was synthesized according to the methodology of Example B, substituting an equivalent amount of 3-amino-5-trifluoromethyl benzoic acid [which was synthesized by reduction of 3-nitro-5-trifluoromethyl benzoic acid (Lancaster) in ethanol with 10% Pd/C under 50 psi H$_2$ for 4 hours] for 3-aminobenzoic acid.

EXAMPLE D

3-Guanidino-5-trifluoromethylbenzoic Acid, Hydrochloride

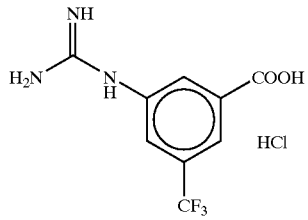

The title compound was synthesized according to the methodology of Example A, substituting an equivalent amount of 3-amino-5-trifluoromethylbenzoic acid (see Example C) for 3-aminobenzoic acid.

EXAMPLE E

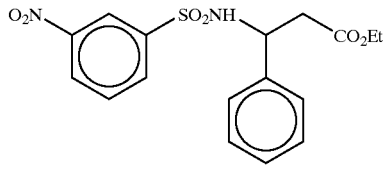

In a dried flask under nitrogen at 0° was dissolved 3-nitrobenzene sulfonyl chloride (2.2 g) (Aldrich) in methylene chloride (25 ml). A solution of β-phenyl alanine ethyl ester hydrochloride (2.3 g), triethylamine (2.3 g) and methylene chloride (25 ml) was added at a rate so as not to allow the temperature to rise above 20°. The reaction mixture was stirred at room temperature for 1 hour and then partitioned between methylene chloride and water. The aqueous portion was extracted several times with additional methylene chloride and the combined organic extracts were washed with saturated sodium chloride solution, dried ($Na_2SO_4$), concentrated and purified on a silica gel column eluting with 40% ethyl acetate–60% hexane to afford 3.3 g of white solid.

NMR was consistent with the proposed structure.

EXAMPLE F

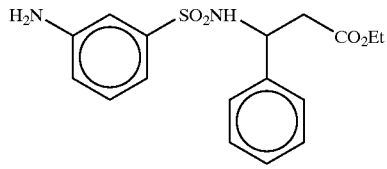

A solution of the product from Example E (3.2 g) in dimethyl formamide (30 ml) was hydrogenated under a hydrogen atmosphere at room temperature for 16 hours using 4% palladium on carbon (300 mg). The reaction mixture was concentrated and purified on a silica gel column using 1:1 ethyl acetate:hexane as eluant to afford 1.6 g of a viscous golden oil. NMR was consistent with the proposed structure.

EXAMPLE G

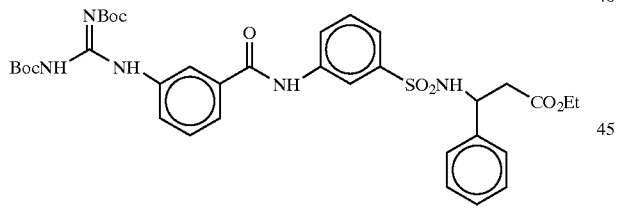

To a solution of 3-bis-boc-guanidine benzoic acid (266 mg) and N-methylmorpholine (76 mg) (Fluka) in DMF (3 ml) at 0° under nitrogen was added a solution of isobutylchloroformate (96 mg) (Aldrich) in DMF (2 ml) in one portion.

The reaction mixture was stirred for 30 minutes and then a solution of the product from Example F (250 mg) and DMF (2 ml) was added in one portion. The reaction mixture was stirred at room temperature for 2 days and then the solvent was removed in vacuo. The residue was purified on a silica gel column using 30% ethyl acetate—70% hexane as eluant to afford 95 mg of white solid. NMR was consistent with the proposed structure.

EXAMPLE 1

Synthesis of β-[[[3-[[[3-[(Aminoiminomethyl)amino]phenyl]carbonyl]amino]phenyl]sulfonyl]amino]-benzenepropanoic Acid, Trifluoroacetate Salt

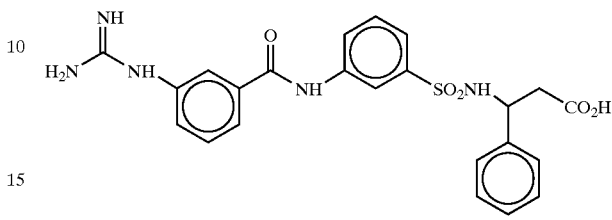

A solution of the product from Example G (90 mg), 1,4 dioxane (2.5 ml) and 6N hydrochloric acid (2.5 ml) was stirred at room temperature for 17 hours. The solvent was removed in vacuo and the residue was purified via reverse phase HPLC using a water (0.5% TFA) and acetonitrile gradient as eluant to afford 64 mg of white solid. NMR was consistent with the proposed structure.

Analysis Calculated for $C_{23}H_{23}N_5O_5S \cdot 2.5CF_3CO_2H$; C, 43.87; H, 3.35; N, 9.14; S, 4.18. Found: C, 43.45; H, 3.30; N, 9.16; S, 4.47.

The compounds of this invention and the following Examples 2–9 were prepared according to the methodology that follows:

EXAMPLE H

General Procedure for the Following Amino Esters

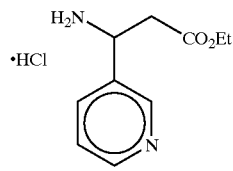

A slurry of 3-pyridinecarboxaldehyde (5.0 gm, 46.7 mmol), malonic acid (5.83 gm, 56 mmol), and ammonium acetate (4.32 gm, 56 mmol) in isopropanol (50 mL) was heated to reflux under a nitrogen atmosphere for 2–3 hours. The reaction mixture was cooled to room temperature and the solids collected by vacuum filtration. The solids were washed on the filter with hot isopropanol (50 mL) and diethyl ether (50 mL) and then dried overnight under vacuum. The crude acid was dissolved in ethanol (50 mL) and anhydrous hydrogen chloride gas was passed through the ethanol solution for 30 minutes. The reaction mixture was then concentrated in vacuo and the remaining white solids were triturated with diethyl ether (50 mL). The white solids were collected and dried under vacuum to afford 5.85 gm (70%) of the amino ester. $^1$H NMR was consistent with the expected product.

EXAMPLE I

Procedure for the Following Amino Ester

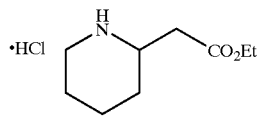

2-Pyridylacetic acid hydrochloride (10 gm, 57.6 mmol) was subjected to hydrogenation conditions ($PtO_2$ in AcOH solvent, 60 psi, 40° C.) to afford the piperidyl product 8.0 gm (80%). The resulting amino acid was subjected to the above esterification conditions (Example H) to afford 8.32 gm (90%) of product. $^1$H NMR was consistent with the expected product.

EXAMPLE J

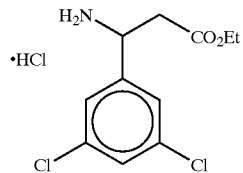

The above compound was prepared using the methodology described in Example H.

EXAMPLE L

General Procedure for the Following Aryl Nitro Compounds

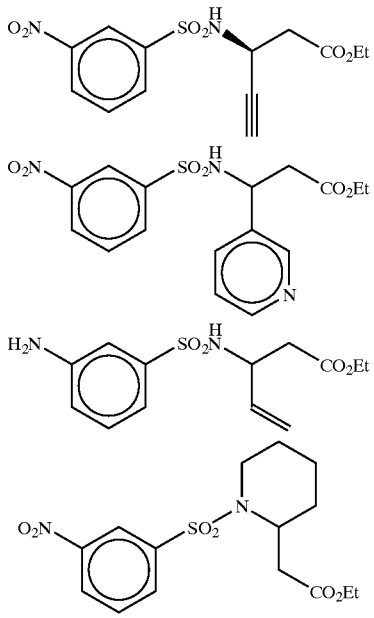

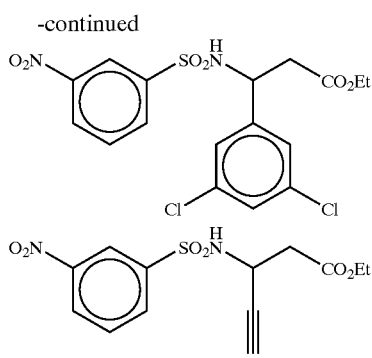

A solution of 3-nitrobenzenesulfonyl chloride (0.65 gm, 2.93 mmol) and the corresponding amino ester prepared via methodology described in Examples H–J [prepared as described in J. Med. Chem., 1995, 38, 2378 or commercially available] in methylene chloride (10 mL) was cooled to 0° C. under a nitrogen atmosphere. To the cooled suspension was then added triethylamine (0.82 mL, 5.86 mmol) and the reaction mixture was allowed to stir at 0° C. for 1 hour, then warmed to room temperature for 2 hours. The reaction mixture was then transferred to a separatory funnel and diluted with 20 mL water. After extraction, the isolated aqueous layer was reextracted with methylene chloride (20 mL). The combined organic extracts were washed with brine (25 mL), dried over $MgSO_4$, vacuum filtered, and concentrated in vacuo to afford a crude white solid. The solids were triturated with 25% ethyl acetate in hexanes (50 mL) and the resulting white crystals were collected and dried overnight under vacuum. Final yield of product was 0.76 gm (79%). $^1$H NMR was consistent with the expected product.

EXAMPLE M

General Procedure for the Following Sulfonamides

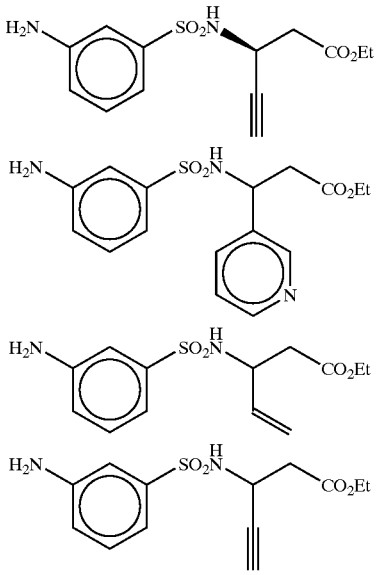

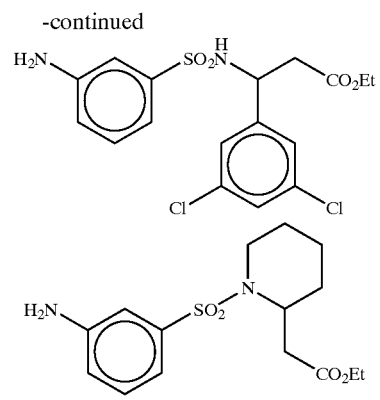

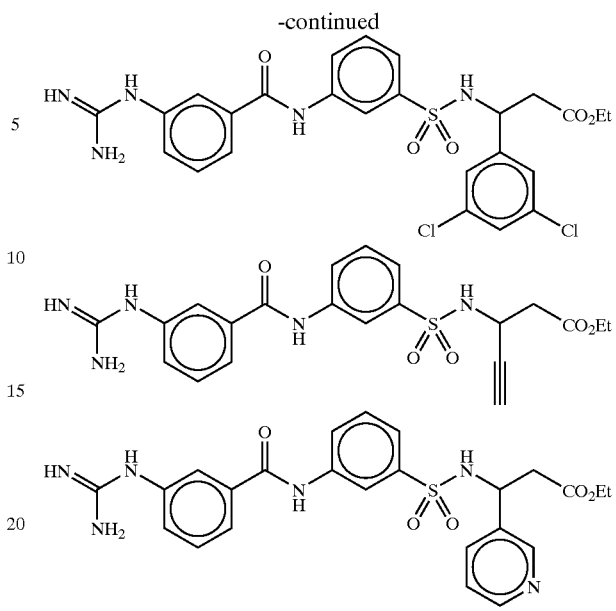

A solution of the nitro sulfonamide from Example L (0.40 gm, 1.23 mmol) and tin (II) chloride.2H$_2$O in ethanol (25 mL) was heated to 80° C. under nitrogen for 2 hours. After cooling to room temperature the reaction mixture was poured into ice water (40 mL) and brought to a basic pH by the slow addition of saturated sodium bicarbonate solution (40 mL). The resulting mixture was then extracted twice with ethyl acetate (2×30 mL). The combined organic extracts were then dried over MgSO$_4$, vacuum filtered, and concentrated in vacuo to afford the amino sulfonamide as an oily product (0.36 gm, 95%). No further purification was necessary. $^1$H NMR was consistent with the expected product.

EXAMPLE N

General Procedure for the Following Esters

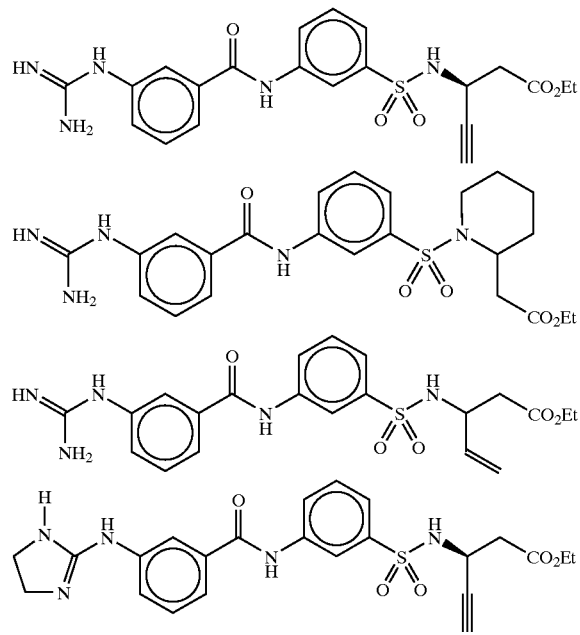

A solution of the compound from Example A (240 mg, 1.11 mmol) in DMAC (5 mL) was cooled to −10° C. under a nitrogen atmosphere. To this solution was then added in sequence isobutyl chloroformate (0.15 mL, 1.17 mmol) followed by N-methyl morpholine (0.13 mL, 1.17 mmol). The resulting mixture was allowed to stir for 30 minutes at −10° C. In a separate flask the sulfonamide was dissolved in DMAC (5 mL) and then transferred to the reaction mixture via syringe. The resulting solution was allowed to warm to room temperature while stirring for 18 hours. The reaction mixture was concentrated in vacuo and the crude product was purified by HPLC to afford the above ester (45%, 284 mg). $^1$H NMR was consistent with the expected product.

The compounds of Examples 2–8 were prepared in the following manner.

A solution of the ethyl ester from Example N (230 mg, 0.40 mmol) in methanol (2 mL), THF (2 mL), and 1 N NaOH (5 mL) was stirred for 2 hours at 20° C. The reaction mixture was then concentrated in vacuo to afford a white residue. Purification of the crude product by HPLC (Method 1) afforded the acid as a white crystalline solid.

Yields:

Example 2 55%

Example 3 57%

Example 4 73%

Example 5 45%

Example 6 52%

Example 7 58%

Example 8 60%

EXAMPLE 2

(±) 3-[[[3-[[[3-[(Aminoiminomethyl)amino]phenyl]-carbonyl]amino]phenyl]sulfonyl]amino]-4-pentynoic Acid

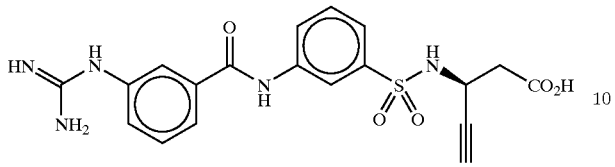

$^1$H NMR (DMSO) δ 12.25 (s, 1H), 10.28 (s, 1H), 10.0 (s, 1H), 8.18 (d, 1H), 8.16 (s, 1H), 8.03 (d, 1H), 7.9 (d, 1H), 7.8 (s, 1H), 7.6 (m, 5H), 7.45 (d, 1H), 4.25 (m, 1H), 3.45 (m, 1H), 3.05 (s, 1H), 2.58 (d, 2H). $^{13}$C NMR (DMSO) 164.8, 155.8, 144.4, 139.4, 135.7, 129.9, 129.5, 127.8, 125.6, 123.7, 121.9, 118.2, 74.7, 41.8, 41.4, 40.0 Hz. Analysis Calc'd for $C_{19}H_{19}N_5O_5S.1.15TFA$; C, 46.41; H, 3.71; N, 12.89; Found: C, 45.67; H, 3.59; N, 12.40.

EXAMPLE 3

(±) 3-[[[3-[[[3-[(Aminoiminomethyl)amino]phenyl]-carbonyl]amino]phenyl]sulfonyl]amino]-4-pentenoic Acid, Trifluoroacetate Salt

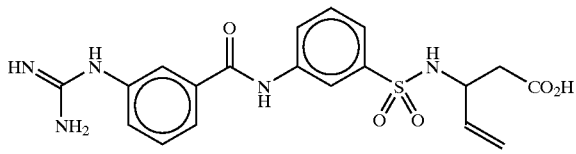

$^1$H NMR (DMSO) δ 12.25 (s, 1H), 10.57 (s, 1H), 10.02 (s, 1H), 8.33 (s, 1H), 8.0 (d, 1H), 7.97 (d, 1H), 7.86 (s, 1H), 7.60 (m, 5H), 7.58 (t, 1H), 7.55 (t, 1H), 7.46 (d, 1H), 5.55 (m, 1H), 4.95 (d, 1H), 4.89 (d, 1H), 4.05 (m, 1H), 2.38 (m, 2H). $^{13}$C NMR (DMSO) 171.2, 164.8, 155.8, 142.1, 139.4, 137.0, 135.7, 129.9, 129.5, 127.8, 125.6, 123.7, 123.5, 121.6, 118.1, 115.7 Hz. Analysis Calc'd for $C_{19}H_{21}N_5O_5S.1.3TFA$; C, 44.75; H, 3.88; N, 12.08; Found: C, 44.94; H, 3.65; N, 12.07.

EXAMPLE 4

(±) β-[[[3-[[[3-[(Aminoiminomethyl)amino]phenyl]-carbonyl]amino]phenyl]sulfonyl]amino]-3,5-dichlorobenzene Propanoic Acid, Trifluoroacetate Salt

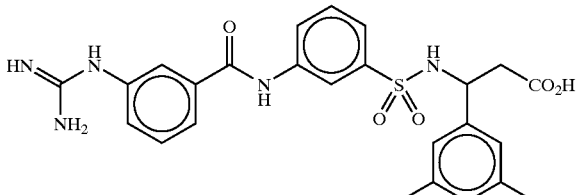

$^1$H NMR (DMSO) δ 10.40 (s, 1H), 9.80 (s, 1H), 8.43 (d, 1H), 8.10 (s, 1H), 7.90 (d, 1H), 7.85 (d, 1H), 7.60 (t, 1H), 7.50 (m, 5H), 7.39 (t, 1H), 7.30 (d, 1H), 7.22 (t, 1H), 7.14 (d, 2H), 4.62 (m, 1H), 2.60 (m, 2H). $^{13}$C NMR (DMSO) 170.63, 164.65, 155.8, 144.0, 141.0, 139.3, 135.8, 135.6, 133.6, 129.8, 129.0, 127.8, 126.7, 125.7, 123.8, 123.1, 117.8, 53.9, 41.8 Hz. Analysis Calc'd for $C_{23}H_{21}Cl_2N_5O_5S.1.2TFA$; C, 44.39; H, 3.26; N, 10.19; Found: C, 44.39; H, 2.92; N, 10.19.

EXAMPLE 5

β-[[[3-[[[3-[(Aminoiminomethyl)amino]phenyl]-carbonyl]amino]phenyl]sulfonyl]amino]pyridine-3-propanoic Acid, tris(Trifluoroacetate) Salt

$^1$H NMR (DMSO) δ 10.22 (s, 1H), 10.0 (s, 1H), 8.58 (d, 1H), 8.45 (s, 1H), 8.42 (d, 1H), 8.15 (s, 1H), 7.90 (d, 1H), 7.85 (m, 2H), 7.60 (m, 4H), 7.47 (d, 1H), 7.37 (m, 3H), 4.75 (m, 1H), 2.77 (m, 2H). $^{13}$C NMR (DMSO) 170.6, 164.7, 155.8, 141.4, 139.3, 135.7, 129.9, 129.4, 127.8, 125.6, 124.3, 123.4, 121.4, 118.0, 52.1, 41.4 Hz. Analysis Calc'd for $C_{22}H_{23}N_6O_5S.3.0TFA.1.0H_2O$; C, 39.87; H, 3.35; N, 9.96; Found: C, 39.84; H, 3.02; N, 10.24.

EXAMPLE 6

1-[[3-[[[3-[(Aminoiminomethyl)amino]phenyl]carbonyl]-amino]phenyl]sulfonyl]piperidine-2-acetic Acid, Trifluoroacetate Salt

$^1$H NMR (DMSO) δ 10.58 (s, 1H), 10.03 (s, 1H), 8.30 (s, 1H), 8.06 (d, 1H), 7.90 (d, 1H), 7.85 (s, 1H), 7.60 (m, 5H), 7.56 (d, 1H), 7.52 (d, 1H), 7.45 (d, 1H), 4.35 (m, 1H), 3.0 (t, 1H), 2.7 (dd, 1H), 2.28 (dd, 1H), 1.45 (m, 6H), 1.15 (2H). Analysis Calc'd for $C_{21}H_{25}N_5O_5S.1.4TFA$; C, 46.17; H, 4.30; N, 11.31; Found: C, 46.02; H, 4.30; N, 11.32.

EXAMPLE 7

3S-[[[3-[[[3-[(4,5-Dihydro-1H-imidazol-2-yl)amino]-phenyl]carbonyl]amino]phenyl]sulfonyl]amino]-4-pentynoic Acid, Trifluoroacetate Salt

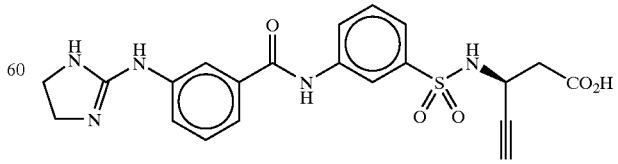

$^1$H NMR (DMSO) δ 12.53 (s, 1H), 10.7 (s, 1H), 10.6 (s, 1H), 8.49 (s, 2H), 8.38 (d, 1H), 8.34 (s, 1H), 8.06 (d, 1H), 7.91 (d, 1H), 7.86 (s, 1H), 7.63 (d, 1H), 7.59 (d, 1H), 7.57 (s, 4H), 7.47 (d, 1H), 4.28 (m, 1H), 3.02 (s, 1H), 2.58 (d, 2H). Analysis Calc'd for $C_{21}H_{21}N_5O_5S.1.3TFA$; C, 46.95; H, 3.72; N, 11.60; Found: C, 46.87; H, 3.61; N, 11.83.

EXAMPLE 8

3-[[[3-[[[3-[(Aminoiminomethyl)amino]phenyl]-carbonyl]amino]phenyl]sulfonyl]amino]-4-pentynoic Acid, Trifluoroacetate Salt

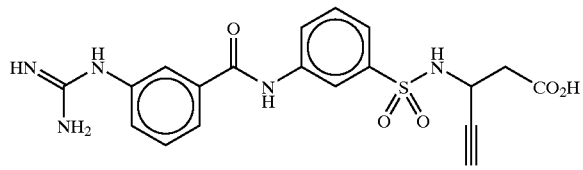

Analysis Calc'd for $C_{19}H_{19}N_5O_5S.1.3TFA$; C, 44.91; H, 3.54; N, 12.12; Found: C, 44.90; H, 3.40; N, 12.34.

EXAMPLE AA

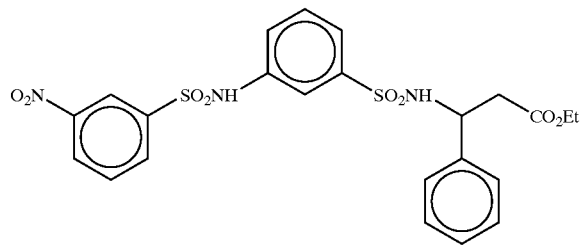

By utilizing the same procedure as described in Example E, the product from Example F was coupled with 3-nitrobenzene sulfonyl chloride to afford the above compound.

NMR data was consistent with the proposed structure.

EXAMPLE BB

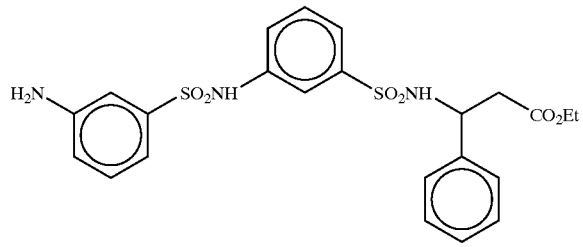

The product from Example AA was hydrogenated and purified in the same manner as described in Example F.

NMR data was consistent with the proposed structure.

EXAMPLE CC

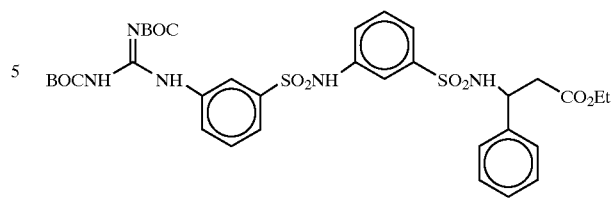

To a solution of the product from Example BB, 1.2 equivalents of bis-t-butoxycarbonyl thiourea and 2.2 equivalents of triethylamine in DMF at 0° under nitrogen was added 1.2 equivalents mercuric chloride in one portion. The reaction was stirred for 30 minutes at 0° and then 30 minutes at room temperature. The reaction was quenched with ethyl acetate, stirred for 30 minutes, and then filtered and concentrated. The crude product was purified on a silica gel column eluting with 25% ethyl acetate–75% hexane to afford the product.

NMR data was consistent with the proposed structure.

EXAMPLE 9

β-[[[3-[[[3-[(Aminoiminomethyl)amino]phenyl]-sulfonyl]amino]phenyl]sulfonyl]amino]phenyl-propanoic Acid, Trifluoroacetate Salt

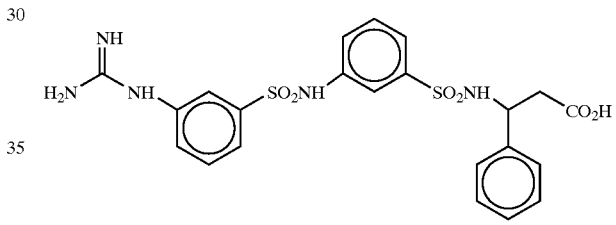

The product from Example CC was treated and purified in the same fashion as described in Example 1.

NMR data was consistent with the proposed structure.
Analysis Calc'd for $C_{22}H_{23}N_5O_6S_2.1.5CF_3CO_2H$: C, 43.61; H, 3.59; N, 10.17; S, 9.31; Found: C, 43.71; H, 3.46; N, 10.34; S, 9.65.

The activity of the compounds of the present invention was tested in the following assays. The results of testing in the assays are tabulated in Table 1.

Vitronectin Adhesion Assay

Materials

Human vitronectin receptor ($\alpha_v\beta_3$) was purified from human placenta as previously described [Pytela et al., *Methods in Enzymology*, 144:475–489 (1987)]. Human vitronectin was purified from fresh frozen plasma as previously described [Yatohgo et al., *Cell Structure and Function*, 13:281–292 (1988)]. Biotinylated human vitronectin was prepared by coupling NHS-biotin from Pierce Chemical Company (Rockford, Ill.) to purified vitronectin as previously described [Charo et al., *J. Biol. Chem.*, 266(3): 1415–1421 (1991)]. Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

Methods

Solid Phase Receptor Assays

This assay was essentially the same as previously reported [Niiya et al., Blood, 70:475–483 (1987)]. The purified human vitronectin receptor ($\alpha_v\beta_3$) was diluted from stock solutions to 1.0 μg/mL in Tris-buffered saline containing 1.0 mM $Ca^{++}$, $Mg^{++}$, and $Mn^{++}$, pH 7.4 ($TBS^{+++}$). The diluted receptor was immediately transferred to Linbro microtiter plates at 100 μL/well (100 ng receptor/well). The plates were sealed and incubated overnight at 4° C. to allow the receptor to bind to the wells. All remaining steps were at room temperature. The assay plates were emptied and 200 μL of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was $1.0 \times 10^{-4}$ M. The competition occurred for two hours after which all wells were washed with a plate washer as before. Affinity purified horseradish peroxidase labeled goat anti-biotin antibody was diluted 1:3000 in $TBS^{+++}$/BSA and 125 μL were added to each well. After 30 minutes, the plates were washed and incubated with OPD/$H_2O_2$ substrate in 100 mM/L Citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and %CV were determined for duplicate concentrations. The mean $A_{450}$ values were normalized to the mean of four maximum-binding controls (no competitor added) (B-MAX). The normalized values were subjected to a four parameter curve fit algorithm [Rodbard et al., Int. Atomic Energy Agency, Vienna, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Ser. No. 08/375,338, Example 1] which is a potent $\alpha_v\beta_3$ antagonist ($IC_{50}$ in the range 3–10 nM) was included on each plate as a positive control.

Purified IIb/IIIa Receptor Assay

Materials

Human fibrinogen receptor ($\alpha_{IIb}\beta_3$) was purified from outdated platelets. (Pytela, R., Pierschbacher, M. D., Argraves, S., Suzuki, S., and Rouslahti, E. "Arginine-Glycine-Aspartic acid adhesion receptors", Methods in Enzymology 144(1987):475–489.) Human vitronectin was purified from fresh frozen plasma as described in Yatohgo T., Izumi, M., Kashiwagi, H., and Hayashi, M., "Novel purification of vitronectin from human plasma by heparin affinity chromatography," Cell Structure and Function 13(1988):281–292. Biotinylated human vitronectin was prepared by coupling NHS-biotin from Pierce Chemical Company (Rockford, Ill.) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", J. Biol. Chem. 266(3) (1991): 1415–1421.) Assay buffer, OPD substrate tablets, and RIA grade BSA were obtained from Sigma (St. Louis, Mo.). Anti-biotin antibody was obtained from Calbiochem (La Jolla, Calif.). Linbro microtiter plates were obtained from Flow Labs (McLean, Va.). ADP reagent was obtained from Sigma (St. Louis, Mo.).

Methods

Solid Phase Receptor Assays

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", Blood 70(1987):475–483. The purified human fibrinogen receptor ($\alpha_{IIb}\beta_3$) was diluted from stock solutions to 1.0 μg/mL in Tris-buffered saline containing 1.0 mM $Ca^{++}$, $Mg^{++}$, and $Mn^{++}$, pH 7.4 ($TBS^{+++}$). The diluted receptor was immediately transferred to Linbro microtiter plates at 100 μL/well (100 ng receptor/well). The plates were sealed and incubated overnight at 4° C. to allow the receptor to bind to the wells. All remaining steps were at room temperature. The assay plates were emptied and 200 μL of 1% RIA grade BSA in $TBS^{+++}$ ($TBS^{+++}$/BSA) were added to block exposed plastic surfaces. Following a 2 hour incubation, the assay plates were washed with $TBS^{+++}$ using a 96 well plate washer. Logarithmic serial dilution of the test compound and controls were made starting at a stock concentration of 2 mM and using 2 nM biotinylated vitronectin in $TBS^{+++}$/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was $1.0 \times 10^{-4}$ M. The competition occurred for two hours after which all wells were washed with a plate washer as before. Affinity purified horseradish peroxidase labeled goat anti-biotin antibody was diluted 1:3000 in $TBS^{+++}$/BSA and 125 μL were added to each well. After 30 minutes, the plates were washed and incubated with ODD/$H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL™ spreadsheet program. The mean, standard deviation, and %CV were determined for duplicate concentrations. The mean $A_{450}$ values were normalized to the mean of four maximum-binding controls (no competitor added) (B-MAX). The normalized values were subjected to a four parameter curve fit algorithm, [Robard et al., Int. Atomic Energy Agency, Vienna, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl] amino]-1-oxoethyl]amino]-3-pyridinepropanoic acid [U.S. Ser. No. 08/375,338, Example 1] which is a potent $\alpha_v\beta_3$ antagonist ($IC_{50}$ in the range 3–10 nM) was included on each plate as a positive control.

Human Platelet Rich Plasma Assays

Healthy aspirin free donors were selected from a pool of volunteers. The harvesting of platelet rich plasma and subsequent ADP induced platelet aggregation assays were performed as described in Zucker, M. B., "Platelet Aggregation Measured by the Photometric Method", *Methods in Enzymology* 169(1989):117–133. Standard venipuncture techniques using a butterfly allowed the withdrawal of 45 mL of whole blood into a 60 mL syringe containing 5 mL of 3.8% trisodium citrate. Following thorough mixing in the syringe, the anti-coagulated whole blood was transferred to a 50 mL conical polyethylene tube. The blood was centrifuged at room temperature for 12 minutes at 200×g to sediment non-platelet cells. Platelet rich plasma was removed to a polyethylene tube and stored at room temperature until used. Platelet poor plasma was obtained from a second centrifugation of the remaining blood at 2000×g for 15 minutes. Platelet counts are typically 300,000 to 500,000 per microliter. Platelet rich plasma (0.45 mL) was aliquoted into siliconized cuvettes and stirred (1100 rpm) at 37° C. for 1 minute prior to adding 50 uL of pre-diluted test compound. After 1 minute of mixing, aggregation was initiated by the addition of 50 uL of 200 uM ADP. Aggregation was recorded for 3 minutes in a Payton dual channel aggregometer (Payton Scientific, Buffalo, N.Y.). The percent inhibition of maximal response (saline control) for a series of test compound dilutions was used to determine a dose response curve. All compounds were tested in duplicate and the concentration of half-maximal inhibition ($IC_{50}$) was calculated graphically from the dose response curve for those compounds which exhibited 50% or greater inhibition at the highest concentration tested; otherwise, the $IC_{50}$ is reported as being greater than the highest concentration tested.

| Example | AvB3 IC50 (nM) | IIb/IIIa IC50 (nM) | Human PRP (μM) |
|---------|----------------|--------------------|----------------|
| 1 | 1.66 | 11.3 | >200 μM |
| 2 | 35.1 | 353 | |
| 3 | 5.34 | 11.6 | |
| 4 | 659 | 987 | |
| 5 | 4.66 | 24.7 | |
| 6 | 183 | 3920 | |
| 7 | 15.0 | 418 | |
| 8 | 11.3 | 38.2 | |
| 9 | 29.3 | 93.6 | |

What is claimed is:

1. A pharmaceutical composition comprising a therapeutically effective amount of a compound of the formula

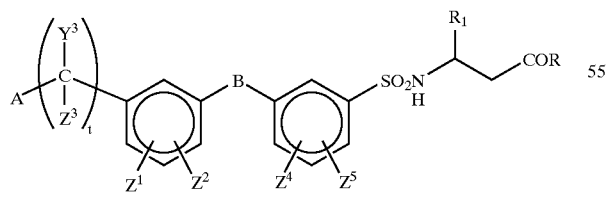

or a pharmaceutically acceptable salt thereof, wherein

B is selected from the group consisting of —$CONR^{50}$— and —$SO_2NR^{50}$—;

A is

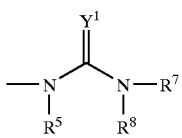

wherein $Y^1$ is selected from the group consisting of N—$R^2$, O, and S;

$R^2$ is selected from the group consisting of H; alkyl; aryl; hydroxy; alkoxy; cyano; nitro; amino; alkenyl; alkynyl; alkyl optionally substituted with one or more substituent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substituent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or $R^2$ taken together with $R^7$ forms a 4–12 membered dinitrogen containing heterocycle optionally substituted with one or more substituent selected from the group consisting of lower alkyl, hydroxy and phenyl;

or $R^2$ taken together with $R^7$ forms a 5 membered heteroaromatic ring;

or $R^2$ taken together with $R^7$ forms a 5 membered heteroaromatic ring fused with a phenyl group;

$R^7$ (when not taken together with $R^2$) and $R^8$ are independently selected from the group consisting of H; alkyl; alkenyl; alkynyl; aralkyl; cycloalkyl; bicycloalkyl; aryl; acyl; benzoyl; alkyl optionally substituted with one or more substituent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, monocyclic heterocycles, fused monocyclic heterocycles; aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethylsulfonyl, alkylsulfonyl, sulfonic acid, sulfonamide, aryl, fused aryl, monocyclic heterocycles, or fused monocyclic heterocycles; monocyclic heterocycles; monocyclic heterocycles optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; —$SO_2R^{10}$ wherein $R^{10}$ is selected from the group consisting of alkyl, aryl and monocyclic heterocycles, all optionally substituted with one or more substituent selected from the group consisting of halogen, haloalkyl, alkyl, alkoxy, cyano, nitro, amino, acylamino, trifluoroalkyl, amido, alkylaminosulfonyl, alkylsulfonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

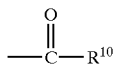

wherein $R^{10}$ is defined above;

or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H, alkyl, alkenyl, alkynyl, benzyl, and phenethyl;

or

A is

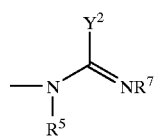

wherein $Y^2$ is selected from the group consisting of alkyl; cycloalkyl; bicycloalkyl; aryl; monocyclic heterocycles; alkyl optionally substituted with aryl which can also be optionally substituted with one or more substituent selected from halo, haloalkyl, alkyl, nitro, hydroxy, hydroxy, alkoxy, aryloxy, aralkoxy, amino, aminoalkyl, carboxyl derivatives, cyano and nitro;

t is an integer 0, 1 or 2;

R is X—$R^3$ wherein X is selected from the group consisting of O, S and $NR^4$, wherein $R^3$ and $R^4$ are independently selected from the group consisting of hydrogen; alkyl; alkenyl; alkynyl; haloalkyl; aryl; arylalkyl; sugars; steroids and in the case of the free acid, all pharmaceutically acceptable salts thereof;

$Y^3$ and $Z^3$ are independently selected from the group consisting of H, alkyl, aryl, cycloalkyl and aralkyl; and a pharmaceutically acceptable carrier.

2. A pharmaceutical composition according to claim 1 of the formula

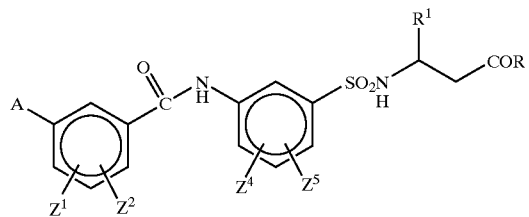

3. A pharmaceutical composition according to claim 2 wherein the compound is selected from the group consisting of β-[[[3-[[[3-[(aminoiminomethyl)amino]phenyl]-carbonyl]amino]phenyl]sulfonyl]amino]-benzenepropanoic acid;

(±) 3-[[[3-[[[3-[(aminoiminomethyl)amino]phenyl]-carbonyl]amino]phenyl]sulfonyl]amino]-4-pentynoic acid;

(±) 3-[[[3-[[[3-[(aminoiminomethyl)amino]phenyl]-carbonyl]amino]phenyl]sulfonyl]amino]-4-pentenoic acid;

(±) β-[[[3-[[[3-[(aminoiminomethyl)amino]phenyl]-carbonyl]amino]phenyl]sulfonyl]amino]-3,5-dichlorobenzene propanoic acid;

β-[[[3-[[[3-[(aminoiminomethyl)amino]phenyl]-carbonyl]amino]phenyl]sulfonyl]amino]-pyridine-3-propanoic acid;

3S-[[[3-[[[3-[(4,5-dihydro-1H-imidazol-2-yl)amino]-phenyl]carbonyl]amino]phenyl]sulfonyl]-amino]-4-pentynoic acid; and 3-[[[3-[[[3-[(aminoiminomethyl)amino]phenyl]-carbonyl]amino]phenyl]sulfonyl]amino]-4-pentynoic acid.

4. A pharmaceutical composition according to claim 1 wherein the compound is β-[[[3-[[[3-[(aminoiminomethyl)amino]-phenyl]sulfonyl]amino]-phenyl]sulfonyl]amino]phenyl-propanoic acid.

5. A method for treating conditions mediated by the $\alpha_v\beta_3$ integrin in a mammal in need of such treatment comprising administering an effective $\alpha_v\beta_3$ inhibiting amount comprising from about 0.01 mg to about 1000 mg per kilogram of body weight of a compound of the formula

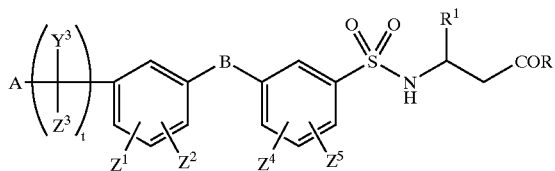

or a pharmaceutically acceptable salt thereof, wherein

B is selected from the group consisting of —$CONR^{50}$— and —$SO_2NR^{50}$—;

A is

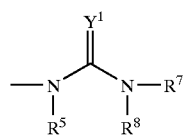

wherein $Y^1$ is selected from the group consisting of N—$R^2$, O, and S;

R² is selected from the group consisting of H; alkyl; aryl; hydroxy; alkoxy; cyano; nitro; amino; alkenyl; alkynyl; alkyl optionally substituted with one or more substitutent selected from lower alkyl, halogen, hydroxyl, haloalkyl, cyano, nitro, carboxyl, amino, alkoxy, aryl or aryl optionally substituted with one or more halogen, haloalkyl, lower alkyl, alkoxy, cyano, alkylsulfonyl, alkylthio, nitro, carboxyl, amino, hydroxyl, sulfonic acid, sulfonamide, aryl, fused aryl, monocyclic heterocycles, or fused monocyclic heterocycles; aryl optionally substituted with one or more substituent selected from halogen, haloalkyl, hydroxy, lower alkyl, alkoxy, methylenedioxy, ethylenedioxy, cyano, nitro, alkylthio, alkylsulfonyl, sulfonic acid, sulfonamide, carboxyl derivatives, amino, aryl, fused aryl, monocyclic heterocycles and fused monocyclic heterocycle; monocyclic heterocycles; and monocyclic heterocycles optionally substituted with one or more substitutent selected from halogen, haloalkyl, lower alkyl, alkoxy, amino, nitro, hydroxy, carboxyl derivatives, cyano, alkylthio, alkylsulfonyl, sulfonic acid, sulfonamide, aryl or fused aryl; or R² taken together with R⁷ forms a 4–12 membered dinitrogen containing heterocycle optionally substituted with one or more substituent selected from the group consisting of lower alkyl, hydroxy and phenyl; or R² taken together with R⁷ forms a 5 membered heteroaromatic ring; or R² taken together with R⁷ forms a 5 membered heteroaromatic ring fused with a phenyl group;

R⁷ (when not taken together with R²) and R⁸ are independently selected from the group consisting of H; alkyl; alkenyl; alkynyl; aralkyl; cycloalkyl; bicycloalkyl; aryl; acyl; benzoyl; alkyl optionally substituted with one or more substiuent selected from lower alkyl, halogen, hydroxy, haloalkyl, cyano, nitro, carboxyl derivatives, amino, alkoxy, thio, alkylthio, sulfonyl, aryl, aralkyl, aryl optionally substituted with one or more substituent selected from halogen, haloalkyl, lower alkyl, alkoxy, methylenedioxy, ethylenedioxy, alkylthio, haloalkylthio, thio, hydroxy, cyano, nitro, carboxyl derivatives, aryloxy, amido, acylamino, amino, alkylamino, dialkylamino, trifluoroalkoxy, trifluoromethyl, sulfonyl, alkylsulfonyl, haloalkylsulfonyl, sulfonic acid, sulfonamide, aryl, fused aryl, moncyclic heterocycles; aryl optionally substituted with one or more substituent selected from halogen, haloalkyl, lower alkyl, alkoxy, aryloxy, amino, nitro, hydroxy, carboxyl derivatives, cyano, alkylthio, alkylsulfonyl, aryl, fused aryl; monocyclic and bicyclic heterocyclicalkyls; —SO₂R¹⁰— wherein R¹⁰ is selected from the group consisting of alkyl, aryl and monocyclic heterocycles, all optionally substituted with one or more substituent selected from the group consisting of halogen, haloalkyl alkyl, alkoxy, cyano, nitro, amino, acylamino, trifluoroalkyl, amido, alkylaminosulfonyl, alkylsufonyl, alkylsulfonylamino, alkylamino, dialkylamino, trifluoromethylthio, trifluoroalkoxy, trifluoromethylsulfonyl, aryl, aryloxy, thio, alkylthio, and monocyclic heterocycles; and

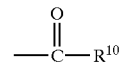

wherein R¹⁰ is defined above; or

NR⁷ and R⁸ taken together form a 4–12 membered mononitrogen containing moncyclic or bicyclic ring optionally substituted with one or more substitutent selected from lower alkyl, carboxyl derivatives, aryl or hydroxy and wherein said ring optionally contains a heteroatom selected from the group consisting of O, N, and S;

R⁵ is selected from the group consisting of H, alkyl, alkenyl, alkynyl, benzyl, and phenethyl; or A is

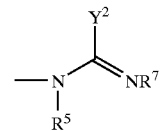

wherein Y² is selected from the group consisting of alkyl; cycloalkyl; bicycloalkyl; aryl; monocyclic heterocycles; alkyl optionally substituted with aryl which can also be optionally substituted with one or more substitutent selected from halo, haloalkyl, alkyl, nitro, hydroxy, alkoxy, aryloxy, aryl, or fused aryl; aryl optionally substituted with one or more substituent selected from halo, haloalkyl, hydroxy, alkoxy, aryloxy, aryl, fused aryl, nitro, methylenedioxy, ethylenedioxy, or alkyl; alkylnyl; alkenyl; —SR⁹ and —OR⁹— wherein R⁹ is selected from the group consisting of H; alkyl; aralkyl; aryl; alkenyl; and alkynyl; or R⁹ taken together with R⁷ forms a 4–12 membered mononitrogen containing sulfur or oxygen containing heterocyclic ring; and R⁵ and R⁷ are as defined above; or Y² (when Y² is carbon) taken together with R⁷ forms a 4–12 membered mononitrogen containing ring optionally substituted with alkyl, aryl, or hydroxy;

Z¹, Z², Z⁴, and Z⁵ are independently selected from the group consisting of H; alkyl; hydroxy; alkoxy; aryloxy; arylalkoxy; halogen; haloalkyl; haloalkoxy; nitro; amino; aminoalkyl; alkylamino; dialkylamino; cyano; alkylthio; alkylsulfonyl; carboxyl derivatives; acetamide; aryl; fused aryl; cycloalkyl; thio; monocyclic heterocycles; fused monocyclic heterocycles; and A, wherein A is defined above;

R⁵⁰ is selected from the group consisting of H and alkyl;

R¹ is selected from the group consisting of H, alkyl, alkenyl, alkynyl, aryl and aryl, optionally substituted with one or more substituent selected form the group consisting of halogen, haloalkyl, hydroxy, alkoxy, aryloxy, aralkoxy, amino, aminoalkyl, carboxyl derivatives, cyano and nitro;

t is an integer 0, 1, or 2;

R is X—R³ wherein X is selected from the group consisting of O, S and NR⁴, wherein R³ and R⁴ are independently selected from the group consisting of hydrogen; alkyl; alkenyl; alkynyl; haloalkyl; aryl; arylalkyl; sugars; steroids and in the case of the free acid, all pharmaceutically acceptable salts thereof; and Y³ and Z³ are independently selected from the group consisting of H, alkyl, aryl, cycloalkyl and arallkyl.

6. A method according to claim 5 wherein the compound is selected from the group consisting of β-[[[3-[[[3-[(aminoiminomethyl)amino]phenyl]-carbonyl]amino]phenyl]sulfonyl]amino]-benzenepropanoic acid;

(±) 3-[[[3-[[[3-[(aminoiminomethyl)amino]phenyl]-carbonyl]amino]phenyl]sulfonyl]amino]-4-pentynoic acid;

(±) 3-[[[3-[[[3-[(aminoiminomethyl)amino]phenyl]-carbonyl]amino]phenyl]sulfonyl]amino]-4-pentenoic acid;

(±) β-[[[3-[[[3-[(aminoiminomethyl)amino]phenyl]-carbonyl]amino]phenyl]sulfonyl]amino]-3,5-dichlorobenzene propanoic acid;

β-[[[3-[[[3-[(aminoiminomethyl)amino]phenyl]-carbonyl]amino]phenyl]sulfonyl]amino]-pyridine-3-propanoic acid;

3S-[[[3-[[[3-[(4,5-dihydro-1H-imidazol-2-yl)amino]-phenyl]carbonyl]amino]phenyl]sulfonyl]-amino]-4-pentynoic acid; and 3-[[[3-[[[3-[(aminoiminomethyl)amino]phenyl]-carbonyl]amino]phenyl]sulfonyl]amino]-4-pentynoic acid.

7. The method according to claim 5 wherein the condition treated is tumor metastasis.

8. The method according to claim 6 wherein the condition treated is tumor metastasis.

9. The method according to claim 5 wherein the condition treated is solid tumor growth.

10. The method according to claim 6 wherein the condition treated is solid tumor growth.

11. The method according to claim 5 wherein the condition treated is angiogenesis.

12. The method according to claim 6 wherein the condition treated is angiogenesis.

13. The method according to claim 5 wherein the condition treated is osteoporosis.

14. The method according to claim 6 wherein the condition treated is osteoporosis.

15. The method according to claim 5 wherein the condition treated is humoral hypercalcemia of malignancy.

16. The method according to claim 6 wherein the condition treated is humoral hypercalcemia of malignancy.

17. The method according to claim 5 wherein the condition treated is smooth muscle cell migration.

18. The method according to claim 6 wherein the condition treated is smooth muscle cell migration.

19. The method according to claim 5 wherein restenosis is inhibited.

20. The method according to claim 6 wherein restenosis is inhibited.

21. A pharmaceutical composition comprising the compound 1-[[3-[[[3-[(aminoiminomethyl)amino]-phenyl]carbonyl]amino]phenyl]sulfonyl]piperidine-2-acetic acid or a pharmaceutically acceptable salt thereof and a pharmaceutically acceptable carrier.

* * * * *